United States Patent [19]
Kato et al.

[11] Patent Number: 5,420,252
[45] Date of Patent: May 30, 1995

[54] HUMAN ANTITHROMBIN III MUTANTS

[75] Inventors: Hiroyuki Kato; Shinji Yoshitake; Suguru Suzuki; Noboru Suzuki; Toshio Seto; Naoko Nagaoka; Yoshiharu Mizui, all of Ibaraki, Japan

[73] Assignee: Eisai Co., Ltd., Tokyo, Japan

[21] Appl. No.: 46,431

[22] Filed: Apr. 9, 1993

[30] Foreign Application Priority Data

Apr. 10, 1992 [JP] Japan .................................. 4-090488
Feb. 22, 1993 [JP] Japan .................................. 5-031855

[51] Int. Cl.⁶ ...................... A61K 38/17; C07K 14/81; C07K 14/435; C12N 15/15
[52] U.S. Cl. ...................... 530/393; 530/395; 435/69.2; 435/172.3; 930/250
[58] Field of Search .................... 435/69.1, 69.6, 172.3, 435/320.1; 514/12; 530/350, 380, 381, 393, 395; 930/10, 250

[56] References Cited

FOREIGN PATENT DOCUMENTS 0384122 8/1990 European Pat. Off. .
0424351 4/1991 European Pat. Off. .
WO91/00291 1/1991 WIPO .

*Primary Examiner*—Robert A. Wax
*Assistant Examiner*—Dian C. Jacobson
*Attorney, Agent, or Firm*—Flynn, Thiel, Boutell & Tanis

[57] ABSTRACT

A novel human antithrombin III (AT III) mutant having a high antithrombin activity in the absence of heparin and effective in the treatment of thrombotic disorders as an anticoagulant, which is obtained by mutating amino acids at the reactive site and the heparin binding site of human AT III into another amino acids with the use of the recombinant DNA technology with the use of a DNA coding for AT III as a template. The invention also relates to a method for mass producing the above-described mutant by incubating a host transformed by an expression vector having the cDNA of the mutant inserted therein.

16 Claims, 10 Drawing Sheets

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:

(A) LENGTH: 1395 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homosapien (ix) FEATURE:
(A) NAME/KEY: CDS
(B) LOCATION: 1..1395
FEATURE:
(A) NAME/KEY: sigpeptide
(B) LOCATION: 1..96
FEATURE:
(A) NAME/KEY: matpeptide
(B) LOCATION: 97..1395

(xi) SEQUENCE DESCRIPTION: SEQ ID NO:1:

| ATG | TAT | TCC | AAT | GTG | ATA | GGA | ACT | GTA | ACC | TCT | GGA | AAA | AGG | AAG | GTT | 48 |
|---|---|---|---|---|---|---|---|---|---|---|---|---|---|---|---|---|
| Met | Tyr | Ser | Asn | Val | Ile | Gly | Thr | Val | Thr | Ser | Gly | Lys | Arg | Lys | Val | |
| -32 | | -30 | | | -25 | | | | | | -20 | | | | | |

| TAT | CTT | TTG | TCC | TTG | CTG | CTC | ATT | GGC | TTC | TGG | GAC | TGC | GTG | ACC | TGT | 96 |
|---|---|---|---|---|---|---|---|---|---|---|---|---|---|---|---|---|
| Tyr | Leu | Leu | Ser | Leu | Leu | Leu | Ile | Gly | Phe | Trp | Asp | Cys | Val | Thr | Cys | |
| | -15 | | | | | -10 | | | | | | -5 | | | | |

| CAC | GGG | AGC | CCT | GTG | GAC | ATC | TGC | ACA | GCC | AAG | CCG | CGG | GAC | ATT | CCC | 144 |
|---|---|---|---|---|---|---|---|---|---|---|---|---|---|---|---|---|
| His | Gly | Ser | Pro | Val | Asp | Ile | Cys | Thr | Ala | Lys | Pro | Arg | Asp | Ile | Pro | |
| 1 | | | | 5 | | | | | 10 | | | | | 15 | | |

| ATG | AAT | CCC | ATG | TGC | ATT | TAC | CGC | TCC | CCG | GAG | AAG | AAG | GCA | ACT | GAG | 192 |
|---|---|---|---|---|---|---|---|---|---|---|---|---|---|---|---|---|
| Met | Asn | Pro | Met | Cys | Ile | Tyr | Arg | Ser | Pro | Glu | Lys | Lys | Ala | Thr | Glu | |
| | | | 20 | | | | | 25 | | | | | 30 | | | |

| GAT | GAG | GGC | TCA | GAA | CAA | AAG | ATC | CCG | GAG | GCC | ACC | AAC | CGG | CGT | GTC | 240 |
|---|---|---|---|---|---|---|---|---|---|---|---|---|---|---|---|---|
| Asp | Glu | Gly | Ser | Glu | Gln | Lys | Ile | Pro | Glu | Ala | Thr | Asn | Arg | Arg | Val | |
| | | 35 | | | | | 40 | | | | | 45 | | | | |

| TGG | GAA | CTG | TCC | AAG | GCC | AAT | TCC | CGC | TTT | GCT | ACC | ACT | TTC | TAT | CAG | 288 |
|---|---|---|---|---|---|---|---|---|---|---|---|---|---|---|---|---|
| Trp | Glu | Leu | Ser | Lys | Ala | Asn | Ser | Arg | Phe | Ala | Thr | Thr | Phe | Tyr | Gln | |
| | 50 | | | | | 55 | | | | | 60 | | | | | |

| CAC | CTG | GCA | GAT | TCC | AAG | AAT | GAC | AAT | GAT | AAC | ATT | TTC | CTG | TCA | CCC | 336 |
|---|---|---|---|---|---|---|---|---|---|---|---|---|---|---|---|---|
| His | Leu | Ala | Asp | Ser | Lys | Asn | Asp | Asn | Asp | Asn | Ile | Phe | Leu | Ser | Pro | |
| 65 | | | | | 70 | | | | | 75 | | | | | 80 | |

| CTG | AGT | ATC | TCC | ACG | GCT | TTT | GCT | ATG | ACC | AAG | CTG | GGT | GCC | TGT | AAT | 384 |
|---|---|---|---|---|---|---|---|---|---|---|---|---|---|---|---|---|
| Leu | Ser | Ile | Ser | Thr | Ala | Phe | Ala | Met | Thr | Lys | Leu | Gly | Ala | Cys | Asn | |
| | | | | 85 | | | | | 90 | | | | | 95 | | |

| GAC | ACC | CTC | CAG | CAA | CTG | ATG | GAG | GTA | TTT | AAG | TTT | GAC | ACC | ATA | TCT | 432 |
|---|---|---|---|---|---|---|---|---|---|---|---|---|---|---|---|---|
| Asp | Thr | Leu | Gln | Gln | Leu | Met | Glu | Val | Phe | Lys | Phe | Asp | Thr | Ile | Ser | |
| | | | 100 | | | | | 105 | | | | | 110 | | | |

| GAG | AAA | ACA | TCT | GAT | CAG | ATC | CAC | TTC | TTC | TTT | GCC | AAA | CTG | AAC | TGC | 480 |
|---|---|---|---|---|---|---|---|---|---|---|---|---|---|---|---|---|
| Glu | Lys | Thr | Ser | Asp | Gln | Ile | His | Phe | Phe | Phe | Ala | Lys | Leu | Asn | Cys | |
| | | 115 | | | | | 120 | | | | | 125 | | | | |

| CGA | CTC | TAT | CGA | AAA | GCC | AAC | AAA | TCC | TCC | AAG | TTA | GTA | TCA | GCC | AAT | 528 |
|---|---|---|---|---|---|---|---|---|---|---|---|---|---|---|---|---|
| Arg | Leu | Tyr | Arg | Lys | Ala | Asn | Lys | Ser | Ser | Lys | Leu | Val | Ser | Ala | Asn | |
| | 130 | | | | | 135 | | | | | 140 | | | | | |

| CGC | CTT | TTT | GGA | GAC | AAA | TCC | CTT | ACC | TTC | AAT | GAG | ACC | TAC | CAG | GAC | 576 |
|---|---|---|---|---|---|---|---|---|---|---|---|---|---|---|---|---|
| Arg | Leu | Phe | Gly | Asp | Lys | Ser | Leu | Thr | Phe | Asn | Glu | Thr | Tyr | Gln | Asp | |
| 145 | | | | | 150 | | | | | 155 | | | | | 160 | |

| ATC | AGT | GAG | TTG | GTA | TAT | GGA | GCC | AAG | CTC | CAG | CCC | CTG | GAC | TTC | AAG | 624 |
|---|---|---|---|---|---|---|---|---|---|---|---|---|---|---|---|---|
| Ile | Ser | Glu | Leu | Val | Tyr | Gly | Ala | Lys | Leu | Gln | Pro | Leu | Asp | Phe | Lys | |
| | | | | 165 | | | | | 170 | | | | | 175 | | |

| GAA | AAT | GCA | GAG | CAA | TCC | AGA | GCG | GCC | ATC | AAC | AAA | TGG | GTG | TCC | AAT | 672 |
|---|---|---|---|---|---|---|---|---|---|---|---|---|---|---|---|---|
| Glu | Asn | Ala | Glu | Gln | Ser | Arg | Ala | Ala | Ile | Asn | Lys | Trp | Val | Ser | Asn | |
| | | | 180 | | | | | 185 | | | | | 190 | | | |

| AAG | ACC | GAA | GGC | CGA | ATC | ACC | GAT | GTC | ATT | CCC | TCG | GAA | GCC | ATC | AAT | 720 |
|---|---|---|---|---|---|---|---|---|---|---|---|---|---|---|---|---|
| Lys | Thr | Glu | Gly | Arg | Ile | Thr | Asp | Val | Ile | Pro | Ser | Glu | Ala | Ile | Asn | |
| | | 195 | | | | | 200 | | | | | 205 | | | | |

| GAG | CTC | ACT | GTT | CTG | GTG | CTG | GTT | AAC | ACC | ATT | TAC | TTC | AAG | GGC | CTG | 768 |

| | | | | | | | | | | | | | | | | |
|---|---|---|---|---|---|---|---|---|---|---|---|---|---|---|---|---|
| Glu | Leu | Thr | Val | Leu | Val | | Val | Asn | Thr | Ile | Tyr | Phe | Lys | Gly | Leu | |
| 210 | | | | | 215 | | | | | | 220 | | | | | |

```
TGG AAG TCA AAG TTC AGC CCT GAG AAC ACA AGG AAG GAA CTG TTC TAC        816
Trp Lys Ser Lys Phe Ser Pro Glu Asn Thr Arg Lys Glu Leu Phe Tyr
225             230                 235                 240

AAG GCT GAT GGA GAG TCG TGT TCA GCA TCT ATG ATG TAC CAG GAA GGC        864
Lys Ala Asp Gly Glu Ser Cys Ser Ala Ser Met Met Tyr Gln Glu Gly
                245                 250                 255

AAG TTC CGT TAT CGG CGC GTG GCT GAA GGC ACC CAG GTG CTT GAG TTG        912
Lys Phe Arg Tyr Arg Arg Val Ala Glu Gly Thr Gln Val Leu Glu Leu
            260                 265                 270

CCC TTC AAA GGT GAT GAC ATC ACC ATG GTC CTC ATC TTG CCC AAG CCT        960
Pro Phe Lys Gly Asp Asp Ile Thr Met Val Leu Ile Leu Pro Lys Pro
        275                 280                 285

GAG AAG AGC CTG GCC AAG GTT GAG AAG GAA CTC ACC CCA GAA GTG CTG       1008
Glu Lys Ser Leu Ala Lys Val Glu Lys Glu Leu Thr Pro Glu Val Leu
    290                 295                 300

CAG GAG TGG CTG GAT GAA TTG GAG GAG ATG ATG CTG GTG GTC CAC ATG       1056
Gln Glu Trp Leu Asp Glu Leu Glu Glu Met Met Leu Val Val His Met
305                 310                 315                 320

CCC CGC TTC CGC ATT GAG GAC GGC TTC AGT TTG AAG GAG CAG CTG CAA       1104
Pro Arg Phe Arg Ile Glu Asp Gly Phe Ser Leu Lys Glu Gln Leu Gln
                325                 330                 335

GAC ATG GGC CTT GTC GAT CTG TTC AGC CCT GAA AAG TCC AAA CTC CCA       1152
Asp Met Gly Leu Val Asp Leu Phe Ser Pro Glu Lys Ser Lys Leu Pro
            340                 345                 350

GGT ATT GTT GCA GAA GGC CGA GAT GAC CTC TAT GTC TCA GAT GCA TTC       1200
Gly Ile Val Ala Glu Gly Arg Asp Asp Leu Tyr Val Ser Asp Ala Phe
        355                 360                 365

CAT AAG GCA TTT CTT GAG GTA AAC GAA GAA GGC AGT GAA GCA GCT GCA       1248
His Lys Ala Phe Leu Glu Val Asn Glu Glu Gly Ser Glu Ala Ala Ala
    370                 375                 380

AGT ACC GCT GTT GTG ATT GCT GGC CGT TCG CTA AAC CCC AAC AGG GTG       1296
Ser Thr Ala Val Val Ile Ala Gly Arg Ser Leu Asn Pro Asn Arg Val
385                 390                 395                 400

ACT TTC AAG GCC AAC AGG CCT TTC CTG GTT TTT ATA AGA GAA GTT CCT       1344
Thr Phe Lys Ala Asn Arg Pro Phe Leu Val Phe Ile Arg Glu Val Pro
                405                 410                 415

CTG AAC ACT ATT ATC TTC ATG GGC AGA GTA GCC AAC CCT TGT GTT AAG       1392
Leu Asn Thr Ile Ile Phe Met Gly Arg Val Ala Asn Pro Cys Val Lys
            420                 425                 430

TAA                                                                    1395
```

( 2 ) INFORMATION FOR SEQ ID NO: 2:

( i ) SEQUENCE CHARACTERISTICS:
        ( A ) LENGTH: 464 amino acids
        ( B ) TYPE: amino acid
        ( D ) TOPOLOGY: linear ( i i ) MOLECULE TYPE:
        ( A ) DESCRIPTION: protein ( x i ) SEQUENCE DESCRIPTION: SEQ ID NO:2:

```
Met Tyr Ser Asn Val Ile Gly Thr Val Thr Ser Gly Lys Arg Lys Val
-32         -30                 -25                 -20

Tyr Leu Leu Ser Leu Leu Leu Ile Gly Phe Trp Asp Cys Val Thr Cys
        -15             -10                  -5

His Gly Ser Pro Val Asp Ile Cys Thr Ala Lys Pro Arg Asp Ile Pro
 1               5                  10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45
```

| | | | | | | | | | | | | | | |
|---|---|---|---|---|---|---|---|---|---|---|---|---|---|---|
| Trp | Glu | Leu | Ser | Lys | Ala | Asn | Ser | Arg | Phe | Ala | Thr | Thr | Phe | Tyr | Gln |
| | 50 | | | | 55 | | | | 60 | | | | | |
| His | Leu | Ala | Asp | Ser | Lys | Asn | Asp | Asn | Asp | Asn | Ile | Phe | Leu | Ser | Pro |
| 65 | | | | | 70 | | | | | 75 | | | | | 80 |
| Leu | Ser | Ile | Ser | Thr | Ala | Phe | Ala | Met | Thr | Lys | Leu | Gly | Ala | Cys | Asn |
| | | | | 85 | | | | | 90 | | | | | 95 | |
| Asp | Thr | Leu | Gln | Gln | Leu | Met | Glu | Val | Phe | Lys | Phe | Asp | Thr | Ile | Ser |
| | | | 100 | | | | | 105 | | | | | 110 | | |
| Glu | Lys | Thr | Ser | Asp | Gln | Ile | His | Phe | Phe | Phe | Ala | Lys | Leu | Asn | Cys |
| | | 115 | | | | | 120 | | | | | 125 | | | |
| Arg | Leu | Tyr | Arg | Lys | Ala | Asn | Lys | Ser | Ser | Lys | Leu | Val | Ser | Ala | Asn |
| | 130 | | | | | 135 | | | | | 140 | | | | |
| Arg | Leu | Phe | Gly | Asp | Lys | Ser | Leu | Thr | Phe | Asn | Glu | Thr | Tyr | Gln | Asp |
| 145 | | | | | 150 | | | | | 155 | | | | | 160 |
| Ile | Ser | Glu | Leu | Val | Tyr | Gly | Ala | Lys | Leu | Gln | Pro | Leu | Asp | Phe | Lys |
| | | | | 165 | | | | | 170 | | | | | 175 | |
| Glu | Asn | Ala | Glu | Gln | Ser | Arg | Ala | Ala | Ile | Asn | Lys | Trp | Val | Ser | Asn |
| | | | 180 | | | | | 185 | | | | | 190 | | |
| Lys | Thr | Glu | Gly | Arg | Ile | Thr | Asp | Val | Ile | Pro | Ser | Glu | Ala | Ile | Asn |
| | | 195 | | | | | 200 | | | | | 205 | | | |
| Glu | Leu | Thr | Val | Leu | Val | Leu | Val | Asn | Thr | Ile | Tyr | Phe | Lys | Gly | Leu |
| | 210 | | | | | 215 | | | | | 220 | | | | |
| Trp | Lys | Ser | Lys | Phe | Ser | Pro | Glu | Asn | Thr | Arg | Lys | Glu | Leu | Phe | Tyr |
| 225 | | | | | 230 | | | | | 235 | | | | | 240 |
| Lys | Ala | Asp | Gly | Glu | Ser | Cys | Ser | Ala | Ser | Met | Met | Tyr | Gln | Glu | Gly |
| | | | | 245 | | | | | 250 | | | | | 255 | |
| Lys | Phe | Arg | Tyr | Arg | Arg | Val | Ala | Glu | Gly | Thr | Gln | Val | Leu | Glu | Leu |
| | | | 260 | | | | | 265 | | | | | 270 | | |
| Pro | Phe | Lys | Gly | Asp | Asp | Ile | Thr | Met | Val | Leu | Ile | Leu | Pro | Lys | Pro |
| | | 275 | | | | | 280 | | | | | 285 | | | |
| Glu | Lys | Ser | Leu | Ala | Lys | Val | Glu | Lys | Glu | Leu | Thr | Pro | Glu | Val | Leu |
| | 290 | | | | | 295 | | | | | 300 | | | | |
| Gln | Glu | Trp | Leu | Asp | Glu | Leu | Glu | Glu | Met | Met | Leu | Val | Val | His | Met |
| 305 | | | | | 310 | | | | | 315 | | | | | 320 |
| Pro | Arg | Phe | Arg | Ile | Glu | Asp | Gly | Phe | Ser | Leu | Lys | Glu | Gln | Leu | Gln |
| | | | | 325 | | | | | 330 | | | | | 335 | |
| Asp | Met | Gly | Leu | Val | Asp | Leu | Phe | Ser | Pro | Glu | Lys | Ser | Lys | Leu | Pro |
| | | | 340 | | | | | 345 | | | | | 350 | | |
| Gly | Ile | Val | Ala | Glu | Gly | Arg | Asp | Asp | Leu | Tyr | Val | Ser | Asp | Ala | Phe |
| | | 355 | | | | | 360 | | | | | 365 | | | |
| His | Lys | Ala | Phe | Leu | Glu | Val | Asn | Glu | Glu | Gly | Ser | Glu | Ala | Ala | Ala |
| | 370 | | | | | 375 | | | | | 380 | | | | |
| Ser | Thr | Ala | Val | Val | Ile | Ala | Gly | Arg | Ser | Leu | Asn | Pro | Asn | Arg | Val |
| 385 | | | | | 390 | | | | | 395 | | | | | 400 |
| Thr | Phe | Lys | Ala | Asn | Arg | Pro | Phe | Leu | Val | Phe | Ile | Arg | Glu | Val | Pro |
| | | | | 405 | | | | | 410 | | | | | 415 | |
| Leu | Asn | Thr | Ile | Ile | Phe | Met | Gly | Arg | Val | Ala | Asn | Pro | Cys | Val | Lys |
| | | | 420 | | | | | 425 | | | | | 430 | | |

( 2 ) INFORMATION FOR SEQ ID NO: 3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (i i) MOLECULE TYPE: DNA (synthetic)

(x i) SEQUENCE DESCRIPTION: SEQ ID NO:3:
TACATGGCCGAAGCTTCGTAATCAT       25

(2) INFORMATION FOR SEQ ID NO: 4:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:4:
CAAAGAATAAGATCTTATTACTTAACACA       29

HUMAN ANTITHROMBIN III MUTANTS

BACKGROUND OF THE INVENTION

1. Field of the Invention

The present invention relates to human antithrombin III (AT III) mutants which are obtained by mutating one or more amino acid(s) in the amino acid sequence of human AT III into another amino acid(s) and exhibit high antiprotease activities even in the absence of heparin. These human AT III mutants are usable as a remedy for thrombotic disorders.

2. Description of the Related Art

Anticoagulant activity of glycosaminoglycans, including heparin, is mediated by antithrombin III (AT III) and heparin colactor II (HC II) contained in the blood. AT III and HC II are serlne protease inhibitors which are called serpins in general. There often has been reported, with respect to AT III, among these substances, that a decrease in the blood AT III level due to a congenital or acquired factor would result in thrombotic disorders. Accordingly, AT III plays a physiologically important role as a factor regulating the blood coagulation system consisting of a series of serine proteases.

It is known that human AT III is a glycoprotein of a molecular weight of approximately 60 kd which is mainly synthesized in the liver and contained in normal plasma at a concentration of about 150 μg/ml and that human AT III inhibits serine proteases participating in coagulation and fibrinolysis systems including thrombin and factor Xa. The primary structure of human AT III has been clarified by the direct determination of its amino acid sequence (see Petersen, T. E. et al., The Physiological Inhibitors of Blood Coagulation and Fibrinolysis, Elsevier Science Publishers, Amsterdam, 43, 1979) and cDNA cloning [see Bock, S. C. et al., Nucl. Acids Res., 10, 8113 (1982); Prochownik, E. V. et al., J. Biol. Chem., 258, 8389 (1982); Chandra, T. et al., Proc. Natl. Acad. Sci. USA, 80, 1845 (1983)]. According to these reports, human AT III is a single-chain glycoprotein consisting of 432 amino acids which is secreted and formed by excising a signal peptide of 32 residues from a precursor protein. It has four N-linked glycosylation sites in the molecule. The carbohydrate content is about 15% of the molecular weight.

Human AT III reacts with a serine protease such as thrombin at a ratio of 1:1 and thus forms a stable complex, thus inhibiting the activity of the protease. It is thought that, in this reaction, a peptide bond between the 393rd Arg residue and the 394th Set residue in the molecule of human AT III is cleaved by the protease and an acyl bond is formed between the terminal Arg residue newly formed and the Ser residue at the active center of the protease. This Arg (393)-Ser (394) sequence is generally referred to as a reactive site.

The protease inhibition by AT III would relatively slowly proceed. When the reaction system contains heparin, however, the reaction is dramatically accelerated. Namely, the addition of heparin elevates the thrombin inhibition rate of AT III by more than 1,000 times. It is thought that this function mechanism proceeds as follows. When heparin binds to a specified site (heparin binding site) in AT III, the higher-order structure of AT III turns into a structure liable to undergo interaction with the protease. At the same time, tile protease binds to the heparin molecule. Thus a ternary complex is apt to be formed. Further, from the physiological viewpoint, it is considered that heparin-like substances existing on the surface of vascular endothelial cells exert similar actions and thus play an important role in the mechanism for regulating the blood coagulation system by AT III.

There have been used so-called anticoagulants for treating and preventing thrombotic disorders induced by various causes. Heparin is one of highly important anticoagulants at present. However, it is reported that serious side effects are sometimes induced by the administration of heparin [see Amerena, J. et al., Adverse Drug React. Acute Poisoning Rev., 9, 1 (1990); Levine, M. N. et al., Semi. in Thrombos. Hemostas., 12, 39 (1986); Kelton, J. G. et al., ibid., 12, 59 (1986) Levine, M. N., ibid., 12, 63 (1986)]. Typical examples of these side effects include hemorrhage, thrombocytopenia, hypoadrenalism, hypersensitiveness, necrosis of the administration site and osteoporosis. When there is a high risk of hemorrhage in the fields of, for example, obstetrics and gynecology or postoperative treatments or in the case of a prolonged administration, heparin should be carefully used. Furthermore, it is reported that heparin promotes inactivation of AT III by elastase of neutrophils in vitro [see Jordan, R. E. et al, Science, 237, 777 (1987); Jordan, R. E. et al., J. Biol. Chem., 264, 10493 (1989)]. Thus care should be taken in the administration of heparin when elastase of neutrophils seemingly relates to the conditions of diseases such as serious infection or septicemia. In addition, the anticoagulant effect of heparin is essentially mediated by AT III and, therefore, can be scarcely expected in the case where blood AT III level is lowered.

Meanwhile, human AT III has been clinically applied to thrombophilia based on congenital AT III deficiency and disseminated intravascular coagulation syndrome (DIC) accompanied by a decrease in AT III in the form of a plasma derived AT III concentrate. As described above, however, AT III exhibits only a slow progressive antithrombin activity in the absence of heparin. Therefore the use of AT III alone is rather a supplementary treatment and its usefulness as an anticoagulant is limited. Thus attempts have been made to use AT III together with heparin or to prepare and use an AT III/heparin complex to thereby improve the usefulness of AT III as an anticoagulant. However, it is obvious that the above-mentioned disadvantages of heparin cannot be overcome even by these methods.

As described above, AT III has two functional sites, namely, the reactive site and the heparin-binding site. A number of reports have revealed that the amino acid sequence around the reactive site carries an important role in the expression of the function as a protease inhibitor as well as in the determination of inhibition specificity against various proteases. In congenital AT III anomalies such as AT III Hamilton wherein Ala at the 382-position has mutated into Thr [see DevraJ-Kizuk, R. et al., Blood, 72, 1518 (1988)], AT III Cambridge I wherein Ala at the 384-position has mutated into Pro [see Perry, P. J. et al., FEBS Lett., 254, 174 (1989)], AT III Glasgow wherein Arg at the 393-position has mutated into His [see Erdjument, H. et al., J. Biol. Chem., 263, 5589 (1988)], AT III Pescara wherein Arg at the 393-position has mutated into Pro [see Lane, D. A. et al., J. Biol. Chem., 264, 10200 (1989)] and AT III Denver wherein Ser at the 394-position has mutated into Leu [see Stephens, A. W. et al., J. Biol. Chem., 262, 1044 (1987)], abnormal AT III molecules each have lost antiprotease activity and patients of these anomalies suffer from thrombotic disorders.

On the other hand, studies on congenital AT III molecule anomalies and results of chemical modification of amino acid residues have revealed amino acids directly relating to the heparin-binding site, namely, binding to heparin. Regarding the molecular anomaly, there have been reported AT III Rouen III wherein Ile at the 7-position has mutated into Asn [see Brennan, S. O. et al., FEBS Lett., 237, 118 (1988)], AT III Rouen IV wherein Arg at the 24-position has mutated into Cys [see Borg, J. Y. et al., FEBS Lett., 266, 163 (1990)], AT III Basel wherein Pro at the 41-position has mutated into Leu [see Chang, J. Y. and Tran, T. H., J. Biol. Chem., 261, 1174 (1986)], AT III Toyama wherein Arg at the 47-position has mutated into Cys [see Koide, T. et al., Proc. Natl. Acad. Sci. USA, 81, 289 (1984)] and AT III Geneva wherein Arg at the 129-position has mutated into Gln [see Gandrille, S. et al., J. Biol. Chem., 265, 18997 (1990)]. Each of these abnormal AT IIIs has a lowered heparin affinity and cannot exert normal physiological functions, thus causing thrombotic disorders. Further, the results of experiments on chemical modification of amino acids suggest that amino acids including Trp at the 49-position, Lys at the 114-position, Lys at the 125-position, Arg at the 129-position, Lys at the 136-position and Arg at the 145-position might directly relate to binding to heparin [see Blackburn, M. N. et al., J. Biol. Chem., 259, 939 (1984); Peterson, C. et al., J. Biol. Chem., 262, 8061 (1987); Sun, X. J. and Chang, J. Y., Biochemistry, 29, 8957 (1990)].

Based on these findings, attempts have been made to improve AT III through substitution of an amino acid(s) of AT III. For example, Zettlemeissl et al. have disclosed a method for producing an AT III mutant having improved properties relating to heparin binding-/heparin activation by mutating an amino acid(s) at the glycosylation site in AT III and another method for producing an AT III mutant having modified enzyme specificities by mutating an amino acid(s) at the reactive site (European Patent Publication-A No. 384122). Further, Dijkema et al. has reported a method for producing an AT III mutant having a modified antithrombin-/antiXa activity by mutating an amino acid(s) at the reactive site (International Publication No. WO 91/00291).

However there has not been found any human AT III mutant which is satisfactory from the clinical viewpoint. It is, therefore, urgently required to construct a human AT III mutant having an elevated activity of inhibiting thrombin or factor Xa in the absence of heparin.

It is an object of the present invention to provide novel human AT III mutants having a high antithrombin activity even in the absence of heparin. It is another object of the present invention to provide a method for mass producing said human AT III mutants by the recombinant DNA technology.

Disclosure of the Invention

Summary of the Invention

At present, it is thought that the mechanism of enchancing the antiprotease activity of AT III by heparin would proceed as follows. First, heparin binds to the heparin binding site of AT III to thereby change the conformation of AT III such that it can more easily react with a protease. At the same time, the protease binds to the same heparin molecule at the above-mentioned heparin binding site, thus elevating the rate of the formation of an AT III/protease complex [see Pierchef, C. H. and Nelsestuen, G. L., J. Biol. Chem., 258, 1086 (1988)]. According to this hypothesis, the change in the configuration at the reactive site induced by the heparin binding to the heparin binding site of AT III is thought to be important in the enhancement of the antiprotease activity. This fact suggests that an AT III mutant exhibiting an enhanced protease activity in the absence of heparin can be constructed by artificially modifying tile amino acid sequence in the neighborhood of the reaction site to thereby change the configuration at the reactive site.

If an AT III mutant having an enhanced antithrombin activity in the absence of heparin can be obtained based on the above-mentioned idea, the action of binding to heparin is seemingly not an important characteristic of this AT III mutant. Thus it is conceivable that a reduction in the affinity for heparin caused by introducing an amino acid substitution into the heparin binding site of the above-described AT III mutant would scarcely affect its function, different from the above-mentioned AT III TOYAMA and AT III GENEVA wherein a mutation in the heparin binding site results in abnormalities in the function. It is rather expected that the clinical usefulness of AT III mutant might be enhanced thereby, since interactions with heparin-like substances existing on the surfaces of vascular endothelial cells are suppressed and thus the half-life in the blood is prolonged and the inactivation with neutrophil elastase is avoided.

Based on this idea, the present inventors have conducted extensive studies in order to improve human AT III. As a result, they have successfully constructed the desired novel human AT III mutants, thus completing tile present invention.

Accordingly, the present invention relates to a human antithrombin III (AT III) mutant obtained by subjecting human AT III to mutation, which has human AT III amino acid sequence described in sequence ID No. 2 except that an amino acid(s) in the sequence is substituted by another amino acid(s) at a region(s) selected from the group consisting of the 11- to 14-positions, the 41- to 47-positions, the 125- to 133-positions and the 384- to 398-positions.

Namely, the present invention relates to an AT III mutant which is a mutated human AT III characterized in that at least one amino acid in each of four regions of the 11- to 14-positions, the 41- to 47-positions, the 125- to 133-positions and the 384- to 398-positions has been substituted, either singly or combinedly, by another amino acid(s), or an AT III mutant characterized in that in the amino acid sequence of human AT III, one or more amino acid(s) selected from among those at the 11- to 14-positions, the 41- to 49-positions, the 121- to 135-positions and the 384- to 398-positions have been substituted by another amino acid(s) and the antithrombin activity in the absence of heparin is elevated as compared with natural AT III.

The human AT III mutant according to the present invention includes the following embodiments:

(1) A human AT III mutant obtained by subjecting human AT III to mutation, which has human AT III amino acid sequence except that an amino acid(s) at a region(s) selected from the group consisting of the 11- to 14-positions, the 41- to 47-positions, the 125- to 133-positions and the 384- to 398-positions is substituted by another amino acid(s) selected from the group consisting of Ala, Gly, Trp, Pro, Leu, Val, Phe, Tyr, Ile, Glu, Ser, Gln, Asn and Arg.

(2) A human AT III mutant obtained by subjecting human AT III to mutation, which has human AT III amino acid sequence except that an amino acid(s) is substituted by another amino acid(s) at the 384- to 398-positions and that an amino acid(s) is substituted by another amino acid(s) at a region(s) selected from the group consisting of the 11- to 14-positions, the 41- to 47-positions and the 125- to 133-positions.

(3) A human AT III mutant obtained by subjecting human AT III to mutation, which has human AT III amino acid sequence except that an amino acid(s) is substituted by another amino acid(s) at the 384- to 398-positions and that an amino acid(s) is substituted by another amino acid(s) at a region(s) selected from the group consisting of the 11- to 14-positions and the 41- to 47-positions.

(4) A human AT III mutant obtained by subjecting human AT III to mutation, which has human AT III amino acid sequence except that an amino acid(s) is substituted by another amino acid(s) at the 384- to 398-positions and that an amino acid(s) is substituted by another amino acid(s) at a region(s) selected from the group consisting of the 11- to 14-positions and the 125- to 133-positions.

(5) A human AT III mutant obtained by subjecting human AT III to mutation, which has human AT III amino acid sequence except that an amino acid(s) is substituted by another amino acid(s) at the 384- to 398-positions and that an amino acid(s) is substituted by another amino acid(s) at a region(s) selected from the group consisting of the 41- to 47-positions and the 125- to 133-positions.

(6) A human AT III mutant obtained by subjecting human AT III to mutation, which has human AT III amino acid sequence except that an amino acid(s) is substituted by another amino acid(s) at the 11- to 14-positions and that an amino acid(s) is substituted by another amino acid(s) at the 384- to 398-positions.

(7) A human AT III mutant obtained by subjecting human AT III to mutation, which has human AT III amino acid sequence except that an amino acid(s) is substituted by another amino acid(s) at the 41- to 47-positions and that an amino acid(s) is substituted another amino acid(s) at the 384- to 398-positions.

(8) A human AT III mutant obtained by subjecting human AT III to mutation, which has human AT III amino acid sequence except that an amino acid(s) is substituted by another amino acid(s) at the 125- to 133-positions and that an amino acid(s) is substituted by another amino acid(s) at the 384- to 398-positions.

(9) A human AT III mutant obtained by subjecting human AT III to mutation, which has human AT III amino acid sequence except that an amino acid(s) is substituted by another amino acid(s) at the 384- to 398-positions.

(10) A human AT Ill mutant obtained by subjecting human AT III to mutation, which has human AT III amino acid sequence except that an amino acid(s) at the 384- to 398-positions is substituted by another amino acid(s) selected from the group consisting of Ala, Pro, Leu, Val, Gly, Arg, Glu and Phe and that an amino acid(s) may be substituted by another amino acid(s) at a region(s) selected from the group consisting of the 11- to 14-positions, the 41- to 47-positions and the 125- To 133-positions.

(11) A human AT III mutant obtained by subjecting human AT III to mutation, which has human AT III amino acid sequence except that an amino acid(s) at the 390- to 392-positions is substituted by another amino acid(s) selected from the group consisting of Ala, Pro. Leu. Val and Phe and that an amino acid(s) may be substituted by another amino acid(s) at a region(s) selected from the group consisting of the 11- to 14-positions, the 41- to 47-positions and the 125- to 133-positions.

(12) A human AT III mutant obtained by subjecting human AT III to mutation, which has human AT III amino acid sequence except that Gly at the 392-position is substituted by Pro and that an amino acid(s) may be substituted by another amino acid(s) at a region(s) selected from the group consisting of the 11- to 14-positions, the 41- to 47-positions and the 125- to 133-positions.

(13) A human AT III mutant obtained by subjecting human AT III to mutation, which has human AT III amino acid sequence except that a substitution selected from the group consisting of a substitution of Ile at the 390- position into Ala, a substitution of Ala at the 391-position into Phe, Val or Leu and a substitution of Gly at the 392-position into Pro is present and that an amino acid(s) may be substituted by another amino acid(s) at a region(s) selected from the group consisting of the 11- to 14-positions, the 41- to 47-positions and the 125- to 133-positions.

(14) A human AT III mutant obtained by subjecting human AT III to substitution, which has human AT III amino acid sequence except that a substitution selected from the group consisting of a substitution of Ala at the 384-position into Gly, a substitution of Ala at the 387-position into Phe, a substitution of Val at the 389-position into Pro, a substitution of Pro at the 397-position into Arg and a substitution of Asn at the 398-position into Glu or Alg is present and that an amino acid(s) may be substituted by into another amino acid(s) at a region(s) selected from the group consisting of the 11- to 14-positions, the 41- to 47-positions and the 125- to 133-positions.

(15) A human AT III mutant obtained by subjecting human AT III to mutation, which has human AT III amino acid sequence except that a substitution selected from the group consisting of a substitution of Lys at the 11- position into Ile, a substitution of Asp at the 14-position into Set is present and that an amino acid(s) may be substituted by another amino acid(s) at a region(s) selected from the group consisting of the 41- to 47-positions, the 125- to 133-positions and the 384- to 398-positions.

(16) A human AT III mutant obtained by subjecting human AT III to mutation, which has human AT III amino acid sequence except that a substitution selected from the group consisting of a substitution of Lys at the 11- position into Ile and a substitution of Asp at the 14-position into Ser, and, another substitution selected from the group consisting of a substitution of Ile at the 390- position into Ala, a substitution of Ala at the 391-position into Phe, Val or Leu and a substitution of Gly at the 392-position into Pro are present, and that an amino acid(s) may be substituted by another amino acid(s) at a region(s) selected from the group consisting of the 41- to 47-positions and the 125- to 133-positions.

(17) A human AT III mutant obtained by subjecting human AT III to mutation, which has human AT III amino acid sequence except that a substitution selected from the group consisting of a substitution of Lys at the 125-position into Gln, a substitution of Arg at the 129-position into Gln, a substitution of Arg at the 132-position into Gln and a substitution of Lys at the 133-position into Asn or Gln is present and that an amino acid(s) may be substituted by another amino acid(s) at a region(s) selected from the group consisting of the 11- to 14-positions, the 41- to 47-positions and the 384- to 398-positions.

(18) A human AT III mutant obtained by subjecting human AT III to mutation, which has human AT III amino acid sequence except that a substitution selected from the group consisting of a substitution of Lys at the 125-position into Gln, a substitution of Arg at the 129-position into Gln, a substitution of Arg at the 132-position into Gln and a substitution of Lys at the 133-position into Ash or Gln, and, another substitution selected from the group consisting of a substitution of Ile at the 390-position into Ala, a substitution of Ala at the 391-position into Phe, Val or Leu and a substitution of Gly at the 392-position into Pro are present, and that an amino acid(s) may be substituted by another amino acid(s) at a region(s) selected from the group consisting of the 11- to 14-positions and the 41- to 47-positions.

(19) A human AT III mutant obtained by subjecting human AT III to mutation, which has human AT III amino acid sequence except that Gly at the 392-position is substituted by Pro.

(20) A human AT III mutant obtained by subjecting human AT III to mutation, which has human AT III amino acid sequence except that Ala-Gly at the 391- to 392-positions is substituted by Phe-Pro.

(21) A human AT III mutant obtained by subjecting human AT III to mutation, which has human AT III amino acid sequence except that Ile-Ala at the 390- to 392-positions is substituted by Ala-Leu.

(22) A human AT III mutant obtained by subjecting human AT III to mutation, which has human AT III amino acid sequence except that Lys at the 125-position is substituted by Gln and Ala-Gly at the 391- to 392-positions is substituted by Phe-Pro.

(23) A human AT III mutant obtained by subjecting human AT III to substitution, which has human AT III amino acid sequence except that Arg-Lys at the 132- to 133-positions is substituted by Gln-Asn and Ile-Ala at the 390- to 391-positions is substituted by Ala-Leu.

(24) A human AT III mutant obtained by subjecting human AT III to substitution, which has human AT III amino acid sequence except that Arg-Lys at the 132- to 133-positions is substituted by Gln-Asn and Ala-Gly at the 391- to 392-positions is substituted by Phe-Pro.

(25) A human AT III mutant obtained by subjecting human AT III to mutation, which has human AT III amino acid sequence except that Lys at the 133-position is substituted by Asn and Ala-Gly at the 391- to 392-positions is substituted by Phe-Pro.

The present invention includes human AT III mutants which are obtained by substituting an amino acid(s) constituting natural human AT III with another amino acid(s) at a desired position(s).

Each of these human AT III mutants is expressed and produced by using animal cells as a host. As will be described hereinbelow, the mutants thus obtained exhibit elevated antithrombin activities in the absence of heparin as compared with a plasma derived human AT III concentrate or a natural recombinant human AT III. Further, these mutants exert improved drug efficacys in tests with the use of animals as compared with the plasma derived human AT III concentrate. Thus it is expected that they are highly useful for clinical purposes.

The present invention also relates to a DNA coding for the human AT III mutant according to the present invention, an expressible vector which has a DNA containing part or the whole of the DNA sequence coding for the human AT III mutant according to the present invention, a transformant which is obtained by subjecting host cells to transformation with the above-described expressible vector and a method for producing a human AT III mutant which comprises incubating the above-described transformant and recovering the human AT III mutant produced by the transformant from the culture.

The present invention further relates to a drug composition for thrombotic disorders which contains the human AT III mutant according to the present invention and pharmaceutically acceptable carriers, a use of the human AT III mutant according to the present invention for the making of a medicament for treating thrombotic disorders, and a method for treating thrombotic disorders which comprises administering a pharmaceutically effective amount of the human AT III mutant according to the present invention to a patient suffering from the thrombotic disorders.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will be described hereinafter in detail.

The term "AT III" means human AT III in the following description.

DETAILED DESCRIPTION OF THE INVENTION

1) Isolation of cDNA coding for AT III

Since AT III is mainly synthesized in the liver, a commercially available human liver cDNA library (λgt 11, available from Clonetech) may be used for the isolation of cDNA coding for AT III. Cloning can be effected by a publicly known method. For example, the plaque hybridization method with the use of a synthetic oligonucleotide corresponding to AT III amino acid sequence as a probe [see Sambrook, J. et al., Molecular Cloning, Cold Spring Harbor Laboratory (1989)] may be used therefor.

The clones thus obtained are subcloned into a plasmid such as pUC 18, if required. The nucleotide sequence of cDNA thus obtained can be determined and estimated by the Maxam-Gilbert method [see Maxam, A.M. and Gilbert, W., Proc. Natl. Acad. Sci. USA, 74, 560 (1977)] or the dideoxy method [Sanger, F., Science, 214, 1205 (1981)]. The nucleotide sequence of the coding region of AT III cDNA thus obtained and the amino acid sequence deduced therefrom are given in SEQ ID. No. 1 in the sequence listing. The amino acid sequence was also described in SEQ ID No. 2 in sequence listing.
Method for site-directed mutagenesis Examples of the method for site-directed mutagenesis include a method of Zoller et al. [see Zoller, M. and Smith, M, Methods in Enzymology, 100, 468 (1983)], the one of Kramer et al. [see Kramer, W. and Fritz, H-J, Methods in Enzymology, 154, 350 (1987)] and the one of Vandeyar et al. [see Vandeyar et al., Gene, 65,129 (1988)].

In the method of Kramer et al., which is called the gapped duplex method, amber mutants of M13 phage such as M13tv18 and M13tv19 are usable as a vector. A DNA coding for AT III is cloned into these vectors. The single-stranded DNA thus obtained and a double-stranded DNA fragment of M13 free from amber mutation (a vector fragment obtained by cleaving M13mpP with Pvu II) are denatured and subjected to degenerative annealing to thereby give a gapped duplex DNA. Next, this DNA is hybridized with a synthetic oligonucleotide having the substitution to be introduced thereinto. After filling up the gap by treating with DNA polymerase and DNA ligase, it was transfected into E. coli mutS strain (BMH71-18 mutS). Then a nonamber phage capable of growing exclusively in supO E. coli is selected. Thus a phage having the desired mutation introduced thereinto can be efficiently obtained. In a practical operation, a commercially available kit (Mutan-G, manufactured by Takara Shuzo Co., Ltd.) may be used. On the other hand, the method of Vandeyar et al. is effected as follows. A single-stranded DNA of M13, into which a DNA coding for AT III has been cloned, is hybridized with an oligonucleotide having the mutation to be introduced. By using it as a template, dATP, dGTP, dTTP and 5-methyl-dCTP are used as substrates and treated with T7 DNA polymerase. The double-stranded DNA thus formed is treated with T4 DNA ligase to thereby give a closed-circular double-stranded DNA. Next, this double-stranded DNA is treated with a restriction enzyme Msp1 and then with exonuclease III. Thus a circular single-stranded DNA exclusively consisting of a strand having the mutation introduced thereinto is obtained. Then it is transfected into an E. coli (SDM strain) free from any restriction system specific for methylated DNA. Thus the desired clone can be efficiently obtained. In the case of this method, a commercially available kit may be used in practice (T7-GEN In Vitro Mutagenesis Kit, manufactured by United States Biochemical Corporation). The synthetic oligonucleotide having the mutation to be introduced can be synthesized by the phosphoramidite method with the use of a DNA synthesizer (Model 380 A. manufactured by ABI). 3) Preparation of template for introducing AT III cDNA mutation A template for introducing substitution is prepared by inserting restriction sites before and after the coding region of the AT III eDNA obtained in the item 1). The restriction enzymes may be selected from among publicly known ones. In the case of the present invention, a Hind III restriction site was inserted immediately before the coding region of the AT III cDNA while a Bgl II restriction site was inserted immediately thereafter.

First, a plasmid containing the AT III cDNA obtained in the item 1) described above is cleaved with EcoR I and thus a Fragment of 1.5 kb including the whole AT III coding region is obtained. This fragment is inserted into a llinearized product obtained by cleaving the RF (Replicatire Form, a double-stranded DNA) of phage M13tv18 with EcoR I.

Among the clones titus obtained, a single-stranded DNA containing the sense strand of AT III is used as a template. In accordance with the method of Kramer et al., two synthetic oligonucleotides containing the restriction sites of Hind III and Bgl II respectively are used as primers and the restriction sites are inserted before and after the coding region of the AT III cDNA.

Subsequently, a fragment containing the AT III cDNA sequence obtained from the clone is inserted into an appropriate plasmid to thereby construct a template for introducing substitution.

In the case of the present invention, a template for introducing substitution can be prepared by inserting the DNA fragment of about 1.5 kb containing the whole AT III coding region, which is obtained by cleaving the above-mentioned clone with Hind III and EcoR I, into the plasmid M13tv19 RF or M13mp19 cleaved with the same enzymes.

Further, the AT III cDNA has a Sac I restriction site (the base part at the 721- to 726-positions in SEQ. ID No. 1) whereby the reactive site can be separated from the heparin binding site. Accordingly, the N-terminal side of AT III obtained by cleaving the above-mentioned clone with Hind III and Sac I, namely, the DNA fragment containing the heparin binding site is inserted into the plasmid M13tv19 or M13mp19 cleaved with the same enzymes. Thus a template for introducing substitution into the heparin binding site can be prepared.

Regarding the reactive site, a similar operation can be carried out by using EcoR I and Sac I.
4) Introduction of substitution into the desired site In the amino acid sequence of AT III, an amino acid at a desired position can be substituted by another desired amino acid (hereinafter referred to as the desired amino acid) in accordance with the above-mentioned publicly known methods by using a synthetic oligonucleotide containing a DNA coding for the desired amino acid and an appropriate plasmid described in the item 3) as a template. When Gly at the 392-position in AT III is to be substituted by Pro, for example, the AT1R oligonucleotide given in Table 1 may be used. In order to substitute Ala-Gly at the 391- to 392-positions with Phe-Pro, the AT5R oligonucleotide listed in Table 1 may be used. When a number of amino acids separately located are to be mutated, a number of mutations can be introduced by successively effecting tile operations for introducing the mutations one by one.

Typical examples of oligonucleotides employed in the present invention are listed in Tables 1 and 2. Amino acid mutation positions and desired amino acids are listed in Tables 3 and 4. Base codes coding for the desired amino acids are not restricted to those listed in Tables 1 and 2 but any codon may be used therefor so long as it codes for the desired amino acid.

TABLE 1

Nucleotide sequence of synthetic oligonucleotide for introducing AT III mutation, amino acid to be mutated and position thereof

| Oligonucleotide | Nucleotide sequence | Amino acid to be mutated and its position |
|---|---|---|
| AT1R | 5' GTTTAGCGACCGCGGAGCAATCAC 3' | Gly392 →Pro |
| AT5R | 5' GGGGTTTAGCGACCGCGGAAAAATCACAACAGC 3' | Ala391 →Phe Gly392 →Pro |
| AT7R | 5' TAGCGAACGGCCGACAGCCACAACAGCGGT 3' | Ile390 →Ala Ala391 →Val |

TABLE 1-continued

Nucleotide sequence of synthetic oligonucleotide for introducing AT III mutation, amino acid to be mutated and position thereof

| Oligonucleotide | Nucleotide sequence | Amino acid to be mutated and its position |
|---|---|---|
| AT9R | 5' CAGCGGTACT<u>GCC</u>AGCTGCTTC 3' | Ala384 →Gly |
| AT19R | 5' ACGGCCAGCAAT<u>CGG</u>AACAGCGGTACT 3' | Val389 →Pro |
| AT24R | 5' AATCACAAC<u>AAA</u>GGTACTTGCAG 3' | Ala387 →Phe |
| AT26R | 5' GTTTAGCGAACG<u>CGGAAT</u>AATCACAACAGC 3' | Ala391 →Ile Gly392 →Pro |
| AT27R | 5' GTTTAGCGAACG<u>CGGACC</u>AATCACAACAG 3' | Ala391 →Gly Gly392 →Pro |
| AT28R | 5' GTTTAGCGAACG<u>CGGATA</u>AATCACAACAGC 3' | Ala391 →Tyr Gly392 →Pro |
| AT29R | 5' GTTTAGCGAACG<u>CGGCCA</u>AATCACAACAGC 3' | Ala391 →Trp Gly392 →Pro |
| AT30R | 5' GTTTAGCGAACG<u>CGGAAC</u>AATCACAACAG 3' | Ala391 →Val Gly392 →Pro |
| AT34R | 5' TAGCGAACGGCC<u>AATAGC</u>CACAACAGCGGT 3' | Ile390 →Ala Ala391 →Ile |
| AT35R | 5' TAGCGAACGGCC<u>AAGAGC</u>CACAACAGCGGT 3' | Ile390 →Ala Ala391 →Leu |
| AT38R | 5' TAGCGAACGGCC<u>AAGACC</u>CACAACAGCGG 3' | Ile390 →Gly Ala391 →Leu |
| At39R | 5' GTTTAGCGAACG<u>GGGAACAGCC</u>ACAACAGCGGTA 3' | Ile390 →Ala Ala391 →Val Gly392 →Pro |

The underlined part in the nucleotide sequence represents the sequence corresponding to the amino acid to be mutated.

TABLE 2

Nucleotide sequence of synthetic oligonucleotide for introducing AT III mutation, amino acid to be mutated and position thereof

| Oligonucleotide | Nucleotide sequence | Amino acid to be mutated and its position |
|---|---|---|
| AT40R | 5' GTTTAGCGAACG<u>GGGAAAAAG</u>CACAACAGCGGTA 3' | Ile390 →Leu Ala391 →Phe Gly392 →Pro |
| AT46R | 5' GTTTAGCGAACG<u>CGGAAG</u>AATCACAACAGC 3' | Ala391 →Leu Gly392 →Pro |
| AT48R | 5' GTTTAGCGAACG<u>CGGATAAGCC</u>ACAACAGCGGTA 3' | Ile390 →Ala Ala391 →Tyr Gly392 →Pro |
| AT49R | 5' GTTTAGCGAACG<u>CGGCCAAGCC</u>ACAACAGCGGT 3' | Ile390 →Ala Ala391 →Trp Gly392 →Pro |
| AT50R | 5' GTTTAGCGAACG<u>CGGCCAAAGC</u>ACAACCGAGGT 3' | Ile390 →Leu Ala391 →Trp Gly392 →Pro |
| AT2R' | 5' GAAAGTCACCCT<u>CTC</u>GGGGTTTAGCGAAC 3' | Asn398 →Glu |
| AT5R' | 5' TTGAAAGTCACCCT<u>CCT</u>CGGGTTTAGCGAACG 3' | Asn398 →Arg |
| AT6R' | 5' TTGAAAGTCACCCG<u>TCGACG</u>GTTTAGCGAACG 3' | Pro397 →Arg Asn398 →Arg |
| AT1G | 5' CGGCAGTTCAG<u>TTG</u>GGCAAAGAAGAAG 3' | Lys125 →Gln |
| AT2G | 5' GGATTTGTTGGC<u>GTTTTG</u>ATAGAGTCGGCA 3' | Arg132 →Gln Lys133 →Asn |
| AT7G | 5' GATAGAG<u>TTG</u>GCAGTTCAG 3' | Arg129 →Gln |
| AT8G | 5' GGTGGCCTCC<u>AGG</u>ATCTTCTG 3' | Pro 41 →Leu |
| AT9G | 5' GGGATTCATGGGAAT<u>GGA</u>TCGTGGG<u>ATT</u>GCTGTGCAGAT '3 | Lys 11 →Ile Asp 14 →Ser |
| AT1F | 5' GTTGGCTTT<u>TTG</u>ATAGAGTCG 3' | Arg132 →Gln |
| AT2F | 5' TTTGTTGGC<u>GTTT</u>CGATAGAG 3' | Lys133 →Asn |
| AT3F | 5' TTTGTTGGC<u>TTGT</u>CGATAGAG 3 | Lys133 →Gln |

The underlined part in the nucleotide sequence represents the sequence corresponding to the amino acid to be mutated.

TABLE 3

Mutated amino acid in AT III mutant

| Amino acid no. | 11 | 14 | 125 | 129 | 132 | 133 | 384 | | | 390 | | | Reactive site ↓ | 395 | | | | 398 | |
|---|---|---|---|---|---|---|---|---|---|---|---|---|---|---|---|---|---|---|---|
| Natural AT III | Lys | Asp | Lys | Arg | Arg | Lys | Ala | Ser | Thr | Ala | Val | Val | Ile | Ala | Gly | Arg | Ser | Leu | Asn Pro Asn |
| 1R | Lys—Asp—Lys—Arg—Arg Lys—Ala Ser Thr Ala Val Val Ile Ala <u>Pro</u> Arg Ser Leu Asn Pro Asn |
| 5R | Lys—Asp—Lys—Arg—Arg Lys—Ala Ser Thr Ala Val Val Ile <u>Phe</u> <u>Pro</u> Arg Ser Leu Asn Pro Asn |
| 26R | Lys—Asp—Lys—Arg—Arg Lys—Ala Ser Thr Ala Val Val Ile <u>Ile</u> <u>Pro</u> Arg Ser Leu Asn Pro Asn |
| 27R | Lys—Asp—Lys—Arg—Arg Lys—Ala Ser Thr Als Val Val Ile <u>Gly</u> <u>Pro</u> Arg Ser Leu Asn Pro Asn |
| 28R | Lys—Asp—Lys—Arg—Arg Lys—Ala Ser Thr Ala Val Val Ile <u>Tyr</u> <u>Pro</u> Arg Ser Leu Asn Pro Asn |
| 29R | Lys—Asp—Lys—Arg—Arg Lys—Ala Ser Thr Ala Val Val Ile <u>Trp</u> <u>Pro</u> Arg Ser Leu Asn Pro Asn |
| 30R | Lys—Asp—Lys—Arg—Arg Lys—Ala Ser Thr Ala Val Val Ile <u>Val</u> <u>Pro</u> Arg Ser Leu Asn Pro Asn |
| 46R | Lys—Asp—Lys—Arg—Arg Lys—Ala Ser Thr Ala Val Val Ile <u>Leu</u> <u>Pro</u> Arg Ser Leu Asn Pro Asn |
| 39R | Lys—Asp—Lys—Arg—Arg Lys—Ala Ser Thr Ala Val Val <u>Ala</u> <u>Val</u> <u>Pro</u> Arg Ser Leu Asn Pro Asn |
| 40R | Lys—Asp—Lys—Arg—Arg Lys—Ala Ser Thr Ala Val Val <u>Leu</u> <u>Phe</u> <u>Pro</u> Arg Ser Leu Asn Pro Asn |
| 48R | Lys—Asp—Lys—Arg—Arg Lys—Ala Ser Thr Ala Val Val <u>Ala</u> <u>Tyr</u> <u>Pro</u> Arg Ser Leu Asn Pro Asn |
| 49R | Lys—Asp—Lys—Arg—Arg Lys—Ala Ser Thr Ala Val Val <u>Ala</u> <u>Trp</u> <u>Pro</u> Arg Ser Leu Asn Pro Asn |
| 50R | Lys—Asp—Lys—Arg—Arg Lys—Ala Ser Thr Ala Val Val <u>Leu</u> <u>Trp</u> <u>Pro</u> Arg Ser Leu Asn Pro Asn |
| 7R | Lys—Asp—Lys—Arg—Arg Lys—Ala Ser Thr Ala Val Val <u>Ala</u> <u>Val</u> Gly Arg Ser Leu Asn Pro Asn |
| 34R | Lys—Asp—Lys—Arg—Arg Lys—Ala Ser Thr Ala Val Val <u>Ala</u> <u>Ile</u> Gly Arg Ser Leu Asn Pro Asn |
| 35R | Lys—Asp—Lys—Arg—Arg Lys—Ala Ser Thr Ala Val Val <u>Ala</u> <u>Leu</u> Gly Arg Ser Leu Asn Pro Asn |
| 38R | Lys—Asp—Lys—Arg—Arg Lys—Ala Ser Thr Ala Val Val <u>Gly</u> <u>Leu</u> Gly Arg Ser Leu Asn Pro Asn |
| 9R | Lys—Asp—Lys—Arg—Arg Lys—<u>Gly</u> Ser Thr Ala Val Val Ile Ala Gly Arg Ser Leu Asn Pro Asn |
| 19R | Lys—Asp—Lys—Arg—Arg Lys—Ala Ser Thr Ala Val <u>Pro</u> Ile Ala Gly Arg Ser Leu Asn Pro Asn |

TABLE 3-continued

| | Mutated amino acid in AT III mutant | | | | | | | | | | |
|---|---|---|---|---|---|---|---|---|---|---|---|
| Amino acid no. | 11 | 14 | 125 | 129 | 132 | 133 | 384 | 390 | Reactive site ↓ 395 | | 398 |
| Natural AT III | Lys—Asp—Lys—Arg—Arg Lys—Ala | | | | | | | Ser Thr Ala Val Val Ile | Ala Gly Arg Ser Leu Asn Pro | | Asn |
| 24R | Lys—Asp—Lys—Arg—Arg Lys—Ala | | | | | | | Ser Thr <u>Phe</u> Val Val Ile | Ala Gly Arg Ser Leu Asn Pro | | Asn |
| 2R' | Lys—Asp—Lys—Arg—Arg Lys—Ala | | | | | | | Ser Thr Ala Val Val Ile | Ala Gly Arg Ser Leu Asn Pro | | <u>Glu</u> |
| 5R' | Lys—Asp—Lys—Arg—Arg Lys—Ala | | | | | | | Ser Thr Ala Val Val Ile | Ala Gly Arg Ser Leu Asn Pro | | <u>Arg</u> |
| 6R' | Lys—Asp—Lys—Arg—Arg Lys—Ala | | | | | | | Ser Thr Ala Val Val Ile | Ala Gly Arg Ser Leu Asn <u>Arg</u> | | <u>Arg</u> |

TABLE 4

| | Mutated amino acid in AT III mutant | | | | | | | | | | |
|---|---|---|---|---|---|---|---|---|---|---|---|
| Amino acid no. | 11 | 14 | 125 | 129 | 132 | 133 | 384 | 390 | Reactive site ↓ 395 | | 398 |
| Natural AT III | Lys—Asp—Lys—Arg—Arg Lys—Ala | | | | | | | Ser Thr Ala Val Val Ile | Ala Gly Arg Ser Leu Asn Pro | | Asn |
| 1G1R | Lys—Asp—<u>Gln</u>—Arg—Arg Lys—Ala | | | | | | | Ser Thr Ala Val Val Ile | Ala <u>Pro</u> Arg Ser Leu Asn Pro | | Asn |
| 1G5R | Lys—Asp—<u>Gln</u>—Arg—Arg Lys—Ala | | | | | | | Ser Thr Ala Val Val Ile | <u>Phe</u> <u>Pro</u> Arg Ser Leu Asn Pro | | Asn |
| 1G30R | Lys—Asp—<u>Gln</u>—Arg—Arg Lys—Ala | | | | | | | Ser Thr Ala Val Val Ile | <u>Val</u> <u>Pro</u> Arg Ser Leu Asn Pro | | Asn |
| 1G35R | Lys—Asp—<u>Gln</u>—Arg—Arg Lys—Ala | | | | | | | Ser Thr Ala Val Val <u>Ala</u> | <u>Leu</u> Gly Arg Ser Leu Asn Pro | | Asn |
| 2G1R | Lys—Asp—Lys—Arg—<u>Gln Asn</u>—Ala | | | | | | | Ser Thr Ala Val Val Ile | Ala <u>Pro</u> Arg Ser Leu Asn Pro | | Asn |
| 2G5R | Lys—Asp—Lys—Arg—<u>Gln Asn</u>—Ala | | | | | | | Ser Thr Ala Val Val Ile | <u>Phe</u> <u>Pro</u> Arg Ser Leu Asn Pro | | Asn |
| 2G30R | Lys—Asp—Lys—Arg—<u>Gln Asn</u>—Ala | | | | | | | Ser Thr Ala Val Val Ile | <u>Val</u> <u>Pro</u> Arg Ser Leu Asn Pro | | Asn |
| 2G35R | Lys—Asp—Lys—Arg—<u>Gln Asn</u>—Ala | | | | | | | Ser Thr Ala Val Val <u>Ala</u> | <u>Leu</u> Gly Arg Ser Leu Asn Pro | | Asn |
| 1F5R | Lys—Asp—Lys—Arg—<u>Gln</u> Lys—Ala | | | | | | | Ser Thr Ala Val Val Ile | <u>Phe</u> <u>Pro</u> Arg Ser Leu Asn Pro | | Asn |
| 2F5R | Lys—Asp—Lys—Arg—Arg <u>Asn</u>—Ala | | | | | | | Ser Thr Ala Val Val Ile | <u>Phe</u> <u>Pro</u> Arg Ser Leu Asn Pro | | Asn |
| 3F5R | Lys—Asp—Lys—Arg—Arg <u>Gln</u>—Ala | | | | | | | Ser Thr Ala Val Val Ile | <u>Phe</u> <u>Pro</u> Arg Ser Leu Asn Pro | | Asn |
| 7G5R | Lys—Asp—Lys—<u>Gln</u>—Arg Lys—Ala | | | | | | | Ser Thr Ala Val Val Ile | <u>Phe</u> <u>Pro</u> Arg Ser Leu Asn Pro | | Asn |
| 7G30R | Lys—Asp—Lys—<u>Gln</u>—Arg Lys—Ala | | | | | | | Ser Thr Ala Val Val Ile | <u>Val</u> <u>Pro</u> Arg Ser Leu Asn Pro | | Asn |
| 7G35R | Lys—Asp—Lys—<u>Gln</u>—Arg Lys—Ala | | | | | | | Ser Thr Ala Val Val <u>Ala</u> | <u>Leu</u> Gly Arg Ser Leu Asn Pro | | Asn |
| 9G5R | <u>Ile</u> —<u>Ser</u> —Lys—Arg—Arg Lys—Ala | | | | | | | Ser Thr Ala Val Val Ile | <u>Phe</u> <u>Pro</u> Arg Ser Leu Asn Pro | | Asn |
| 9G30R | <u>Ile</u> —<u>Ser</u> —Lys—Arg—Arg Lys—Ala | | | | | | | Ser Thr Ala Val Val Ile | <u>Val</u> <u>Pro</u> Arg Ser Leu Asn Pro | | Asn |
| 9G35R | <u>Ile</u> —<u>Ser</u> —Lys—Arg—Arg Lys—Ala | | | | | | | Ser Thr Ala Val Val <u>Ala</u> | <u>Leu</u> Gly Arg Ser Leu Asn Pro | | Asn |
| 12G5R | Lys—Asp—<u>Gln</u>—Arg—<u>Gln Asn</u>—Ala | | | | | | | Ser Thr Ala Val Val Ile | <u>Phe</u> <u>Pro</u> Arg Ser Leu Asn Pro | | Asn |
| 12G30R | Lys—Asp—<u>Gln</u>—Arg—<u>Gln Asn</u>—Ala | | | | | | | Ser Thr Ala Val Val Ile | <u>Val</u> <u>Pro</u> Arg Ser Leu Asn Pro | | Asn |
| 12G35R | Lys—Asp—<u>Gln</u>—Arg—<u>Gln Asn</u>—Ala | | | | | | | Ser Thr Ala Val Val <u>Ala</u> | <u>Leu</u> Gly Arg Ser Leu Asn Pro | | Asn |
| 127G5R | Lys—Asp—<u>Gln</u>—<u>Gln</u>—<u>Gln Asn</u>—Ala | | | | | | | Ser Thr Ala Val Val Ile | <u>Phe</u> <u>Pro</u> Arg Ser Leu Asn Pro | | Asn |
| 127G30R | Lys—Asp—<u>Gln</u>—<u>Gln</u>—<u>Gln Asn</u>—Ala | | | | | | | Ser Thr Ala Val Val Ile | <u>Val</u> <u>Pro</u> Arg Ser Leu Asn Pro | | Asn |
| 127G35R | Lys—Asp—<u>Gln</u>—<u>Gln</u>—<u>Gln Asn</u>—Ala | | | | | | | Ser Thr Ala Val Val <u>Ala</u> | <u>Leu</u> Gly Arg Ser Leu Asn Pro | | Asn |

5) Combination of mutation in the neighborhood of reactive site and mutation at heparin binding site As described above, AT III cDNA involves a Sac I restriction site which is located between the reactive site and the heparin binding site. Thus a fragment containing the heparin binding site and another one containing the reactive site can be obtained by cleaving a plasmid containing the mutated AT III DNA obtained by the method described in the aforementioned item 4) with Hind III and SacI or Sac I and Bgl II. An AT III mutant DNA, in which both of the reactive and heparin binding sites have mutated, can be prepared by treating an AT III DNA having a mutated reactive site and another AT III DNA having a mutated heparin binding site, respectively, with restriction enzymes to thereby give a DNA fragment having a mutated reactive site and another DNA fragment having a mutated heparin binding site and connecting the mutated DNA fragments with an appropriate plasmid. According to this method, any combination of mutations at these sites can be achieved. Any plasmid can be used as the one to which the mutated DNA fragments are connected so long as it is suitable for the expression thereof in a host. For example, pSV2 and pK4K are usable.

In Table 4, a symbol 2G35R means a mutant obtained by combining a 2G-mutated DNA fragment with a 35R-mutated one.

6) AT III mutant recombinant expression vector and transformant thereof

The DNA coding for the AT III mutant obtained by the above-mentioned method is inserted into an appropriate vector and then the vector obtained is transfected into appropriate host cells. Thus a transformant can be obtained. This transformant is incubated by a conventional method and thus an AT III mutant can be produced in a large amount from the culture.

A DNA coding for an AT III mutant is reconnected to a vector suitable for the expression of the AT III mutant at the downstream of tile promoter of the vector by a publicly known method with the use of a restriction enzyme and DNA ligase. Thus a recombinant expression vector can be constructed. The vector is not particularly restricted, so long as it can be replicated and amplified in a host. Neither the promoter nor the terminator are particularly restricted so long as they correspond to the host to be used in the expression of the nucleotide sequence coding for the AT III mutant. Thus an appropriate combination thereof may be selected depending on the employed host.

The recombinant expression vector thus obtained is transfected into a host by the competent cell method [see Hanahan, D., J. Mol. Biol., 166, 557 (1983)], the calcium phosphate method [see Wiglet, M. et. al., Cell, 11, 222 (1977)] and so on to thereby form a transformant. As the host, E. coli, animal cells, etc. are usable. The transformant thus obtained is incubated in a medium suitable for the host. The incubation may be usually carried out at a temperature of from 20° to 45° C. at a pH value of from 5 to 8 with aeration and stirring, if necessary. The AT III mutant can be separated and purified from the culture by combining publicly known separation and purification methods. Examples of these publicly known methods include salting out, solvent precipitation, dialysis, gel filtration, electrophoresis, ion exchange chromatography, affinity chromatography and reversed phase high performance liquid chromatography. The AT III mutant thus obtained has an elevated antithrombin activity in the absence of heparin and an elevated in vivo antithrombotic action in rats as each compared with natural AT III.

EFFECTS OF THE INVENTION (1) Antithrombin activity

By using a Testzym AT III 2 Kit (manufactured by Daiichi Kagaku Yakuhin), the antithrombin activity of the AT III mutant according to the present invention was measured. Namely, the inhibition activity on thrombin thereof in the absence of heparin was measured by using a synthetic substrate (S-2238) of thrombin. As a control, a plasma derived AT III concentrate (Anthrobin P; manufactured by Hoechst Japan) was employed.

In this measurement, a 50 mM Tris hydrochloride buffer solution (pH 7.5) containing 0.1% of bovine serum albumin and 0.15M of sodium chloride was used. Specimens of various concentrations were reacted with a given amount of thrombin (originated in bovine) at 37° C. for 5 minutes. After the completion of the reaction, the synthetic substrate S-2238 was added and the amount of p-nitroaniline liberated for 2 minutes was determined based on a change in the absorbance at a wavelength of 405 nm. Thus, the remaining thrombin activity was measured. Under these conditions, the AT III mutant concentration at which 50% of the thrombin activity was inhibited (hereinafter referred to as the $IC_{50}$) was calculated.

Table 5 shows the $IC_{50}$ values of mutants. The $IC_{50}$ of the plasma derived AT III concentrate in the absence of heparin was $13.0 \times 10^{-8}$M and that of the natural recombinant AT III was on almost the same level. In contrast, the $IC_{50}$ values of the AT III mutants of the present invention were clearly lower than them, suggesting that the antithrombin activity in the absence of heparin had been elevated.

TABLE 5

| | Antithrombin activity of AT III mutant | | |
|---|---|---|---|
| Specimen | Antithrombin activity $IC_{50} \times 10^{-8}$ (M) | Specimen | Antithrombin activity $IC_{50} \times 10^{-8}$ (M) |
| AT III concentrate | 13.0 | | |
| Natural recombinant AT III | 14.0 | | |
| 1R | 3.0 | | |
| 5R | 1.7 | 38R | 6.1 |
| 26R | 3.1 | 9R | 5.8 |
| 27R | 8.2 | 19R | 8.7 |
| 28R | 2.8 | 24R | 10.0 |
| 29R | 1.8 | 2R' | 3.8 |
| 30R | 2.3 | 5R' | 4.7 |
| 46R | 5.0 | 1G1R | 3.7 |
| 39R | 5.6 | 1G5R | 2.9 |
| 40R | 3.1 | 2G1R | 3.8 |
| 48R | 5.7 | 2G5R | 2.9 |
| 49R | 5.6 | 2G30R | 1.6 |
| 50R | 3.0 | 2G35R | 2.2 |
| 7R | 2.9 | 7G5R | 1.8 |
| 34R | 3.5 | 9G5R | 1.7 |
| 35R | 3.5 | 127G5R | 1.5 |

(2) Affinity for heparin

The affinities for heparin of the AT III mutants according to the present invention were compared and examined by the high performance liquid chromatography method with the use of heparin-5PW (7.5 mm×75 mm; manufactured by Tosoh Corp.). Namely, a 50 mM Tris hydrochloride buffer solution (pH 7.5) was used as a mobile phase and the concentration of sodium chloride was linearly increased from 0M to 2M within 30 minutes at a flow rate of 1 ml/min. The detection was effected based on the absorption at a wavelength of 280 nm and the time required for the elution of each specimen was compared.

As Table 6 shows, the main peak fractions of the AT III and the natural recombinant AT III were eluted, respectively, 22.3 minutes and 23.1 minutes after the intiation of the elution, showing no large difference. Compared with the AT III and the natural recombinant AT III, the mutants having a mutation in the neighborhood of the reactive site showed no remarkable difference. On the other hand, the mutants having mutations in the neighborhood of the reactive site and at the heparin binding site showed each a significantly shortened elution time of the main peak fraction. It was thus confirmed that the introduction of a mutation into the heparin binding site would have lowered the affinity for heparin.

TABLE 6

| Affinity for heparin of AT III mutant (elution time from heparin column) | | | |
|---|---|---|---|
| Specimen | Elution time (min) | Specimen | Elution time (min) |
| AT III concentrate | 22.3 | | |
| Natural recombinant AT III | 23.1 | | |
| 5R | 21.4 | 9R | 22.5 |
| 26R | 21.2 | 19R | 23.2 |
| 28R | 22.5 | 24R | 23.4 |
| 29R | 21.0 | 5R' | 23.6 |
| 30R | 20.4 | 1G1R | 14.0 |
| 46R | 17.4 | 1G5R | 14.3 |
| 40R | 21.0 | 2G1R | 12.5 |
| 48R | 21.6 | 2G5R | 12.9 |
| 7R | 21.9 | 2G30R | 13.0 |
| 35R | 22.1 | 2G35R | 13.1 |

TABLE 6-continued

| Affinity for heparin of AT III mutant (elution time from heparin column) | | | |
|---|---|---|---|
| Specimen | Elution time (min) | Specimen | Elution time (min) |
| 38R | 21.9 | 7G5R | 12.9 |
| | | 127G5R | 10.2 |

(3) Antithrombotic action of AT III mutant

By using a plasma derived AT III concentrate (Anthrobin P; manufactured by Hoechst Japan) and a natural recombinant AT III as controls, the antithrombotic actions of the AT III mutants according to the present invention were measured by the following method.

A method reported by Peters etal. [see Peters, R. F. et al., Thrombosis Haemostasis, 65, 268 (1991)] was modified and employed. Namely, a shunt was formed by cannulating Atom Venous Catheter (4Fr, 3.5 cm, manufactured by Atom) filled with a physiological saline into the carotid arteriovein of a male Sprague-Dawley rat (200–300 g) under anesthesia. After blocking the blood stream, the artery side of the shunt was provided with a pulse wave pickup (MPP-3, manufactured by Nippon Koden) and thus changes in the blood stream were monitored with a polygraph recorder during the test period. A calculated amount of a specimen material was diluted with a physiological saline to give a volume of 1 ml and quickly administered once to the rat via the femoral vein. Then the shunt was opened and the blood was allowed to pass. The time required from the point of opening the shunt to the point of the occlusion of the shunt due to the formation of a thrombus was measured and defined as the occlusion time.

Tables 7 and 8 show the results. It was thus proved that the AT III mutants of the present invention had strong antithrombotic actions as compared with the plasma derived AT III concentrate and the natural recombinant AT III.

TABLE 7

| Antithrombotic action of AT III mutant | | | |
|---|---|---|---|
| Specimen | Dose (mg/kg) | Occlusion time Mean ± SD (min) | Case no. |
| Physiological saline | | 21.4 ± 2.7 | 11 |
| AT III concentrate | 8 | 29.1 ± 8.0 | 9 |
| | 16 | 36.4 ± 11.6 | 8 |
| | 32 | 46.6 ± 14.3 | 8 |
| Natural recombinant AT III | 16 | 39.3 ± 10.5 | 6 |
| | 32 | 49.0 ± 13.7 | 4 |
| 5R | 8 | 46.0 ± 18.6 | 7 |
| | 16 | 65.7 ± 21.0 | 6 |
| 30R | 4 | 35.3 ± 7.1 | 6 |
| | 8 | 43.6 ± 4.7 | 6 |
| | 16 | 52.2 ± 5.3 | 6 |
| 35R | 2 | 34.7 ± 5.8 | 7 |
| | 4 | 39.9 ± 9.4 | 7 |
| | 8 | 61.4 ± 12.6 | 7 |
| 1G5R | 4 | 34.1 ± 8.7 | 8 |
| | 8 | 45.2 ± 10.1 | 6 |
| | 16 | 69.0 ± 25.7 | 6 |
| 2G5R | 4 | 45.7 ± 7.5 | 7 |
| | 8 | 53.6 ± 9.3 | 9 |
| | 16 | 70.6 ± 11.5 | 8 |
| 2G30R | 4 | 35.5 ± 5.5 | 6 |
| | 8 | 45.7 ± 11.2 | 6 |
| | 16 | 53.8 ± 13.7 | 6 |
| 2G35R | 2 | 43.8 ± 6.6 | 6 |
| | 4 | 45.2 ± 5.8 | 6 |
| | 8 | 62.7 ± 28.2 | 6 |

TABLE 8

| Antithrombotic action of AT III mutant | | | |
|---|---|---|---|
| Specimen | Dose (mg/kg) | Occlusion time Mean ± SD (min) | Case no. |
| 1F5R | 4 | 38.3 ± 6.0 | 6 |
| | 8 | 41.3 ± 7.1 | 6 |
| | 16 | 54.7 ± 13.1 | 6 |
| 2F5R | 4 | 39.5 ± 6.1 | 6 |
| | 8 | 47.8 ± 9.5 | 6 |
| | 16 | 59.8 ± 16.1 | 6 |
| 3F5R | 4 | 38.5 ± 6.3 | 6 |
| | 8 | 45.3 ± 5.2 | 6 |
| | 16 | 55.7 ± 4.5 | 6 |
| 7G5R | 4 | 36.5 ± 5.1 | 6 |
| | 8 | 39.7 ± 3.9 | 6 |
| | 16 | 54.2 ± 18.3 | 6 |
| 9G5R | 2 | 38.3 ± 2.7 | 6 |
| | 4 | 38.5 ± 3.1 | 6 |
| | 8 | 49.2 ± 2.8 | 6 |
| 12G5R | 2 | 36.5 ± 6.0 | 6 |
| | 4 | 43.7 ± 2.7 | 6 |
| | 8 | 51.2 ± 6.3 | 6 |
| 127G5R | 2 | 36.0 ± 7.4 | 6 |
| | 4 | 46.8 ± 4.4 | 6 |
| | 8 | 57.0 ± 10.9 | 6 |

These results suggest that the AT III mutants according to the present invention serve as anticoagulants and suppress the formation of thrombi. Thus they are expected to be useful as preventive and therapeutic agents for thrombotic disorders. (4) Effect of AT III mutant on experimental model of disseminated intravascular coagulation (DIC)

By using a plasma derived AT III concentrate as a control, the effects of the AT III mutants according to the present invention on an experimental model of disseminated intravascular coagulation (DIC) were examined by the following method. A method reported by Sugishima et al. [see Tadashi Sugishima et al., Rinsho to Kenkyu, 62, 274 (1985)] was modified and employed. Namely, a model was formed by cannulating an Atom Venous Catheter (3Fr, manufactured by Atom) into the jugular vein of a male Sprague-Dawley rat (200–300 g) under anesthesia and continuously administering tissue thromboplastin (Thromborel S, manufactured by Behringwerke, AG) for an hour. A test specimen was rapidly administered once via the femoral artery of the rat immediately before starting the administration of tissue thromboplastin. Thirty minutes after the completion of the administration of tissue thromboplastin, the blood was sampled via the descending aorta of the rat and 1/10 volume of 3.8% sodium citrate was added thereto. After the sampling, 0.5 ml of the blood was immediately taken in a container for an automatic hemocytometer (manufactured by Toa Iyo Denshi K.K.) and platelets were counted with an H.1 System (manufactured by Technicon). The residual blood was centrifuged (3000 rpm, 10 min) to thereby give the plasma. Then fibrinogen contained in the plasma was determined. The content of fibrinogen in the plasma was measured by the thrombin time method (Fibrinogen B-Test Wako, manufactured by Wako Pure Chemical Industries, Ltd.).

Table 9 shows the results. Thus it was found out that the AT III mutants of the present invention exerted strong effects on a decrease in platelet count and the reduction of plasma fibrinogen level in the experimental DIC model induced with tissue thromboplastin as compared with the plasma derived AT III concentrate. Based on these results, the AT III mutants of the present invention are expected to be useful therapeutic agent for DIC.

TABLE 9

Effect of AT III mutant on experimental DIC model

| Specimen | Dose (mg/kg) | No. of cases | Platelet count (× 10³/μl) Mean ± SD | Amount of plasma fibrinogen (g/l) Mean ± SD |
|---|---|---|---|---|
| Physiological saline (no tissue thromboplastin administered) | | 12 | 952.7 ± 110.6 | 1.95 ± 0.15 |
| Sole administration of tissue thromboplastin | | 12 | 424.1 ± 122.3 | 0.12 ± 0.03 |
| AT III concentrate | 8 | 12 | 527.0 ± 108.8 | 0.17 ± 0.06 |
| | 16 | 11 | 596.6 ± 60.9 | 0.20 ± 0.07 |
| | 32 | 12 | 683.7 ± 128.9 | 0.77 ± 0.41 |
| 1G5R | 4 | 6 | 574.7 ± 54.2 | 0.36 ± 0.42 |
| | 8 | 6 | 729.7 ± 77.6 | 0.99 ± 0.54 |
| 2G5R | 4 | 6 | 618.5 ± 116.1 | 0.21 ± 0.07 |
| | 8 | 6 | 618.2 ± 146.3 | 0.77 ± 0.28 |
| 1F5R | 4 | 6 | 557.2 ± 154.4 | 0.30 ± 0.34 |
| | 8 | 6 | 649.5 ± 112.6 | 0.64 ± 0.39 |
| 2F5R | 4 | 6 | 528.8 ± 89.1 | 0.24 ± 0.08 |
| | 8 | 5 | 659.8 ± 53.6 | 0.63 ± 0.24 |
| 3F5R | 4 | 6 | 487.3 ± 83.4 | 0.16 ± 0.08 |
| | 8 | 6 | 664.5 ± 61.5 | 0.54 ± 0.37 |

This AT III mutant can be orally, topically, intravenously, intramuscularly or subcutaneously administered, among which topical or intravenous administration is preferable. The dose may range from 0.1 to 100 mg/kg and preferably from 0.5 to 20 mg/kg, and is determined depending on the body weight of the patient. It is dissolved in from 1 to 50 ml of a physiological saline and used.

It may be formulated into, for example, wettable powders, solutions, tablets, capsules, powders, suppositories and the like. As carriers for formulating these preparations, pharmaceutically acceptable fillers, disintegrating agents, lubricants and dispersion media commonly employed in the art may be used.

EXAMPLES

Figure 1:
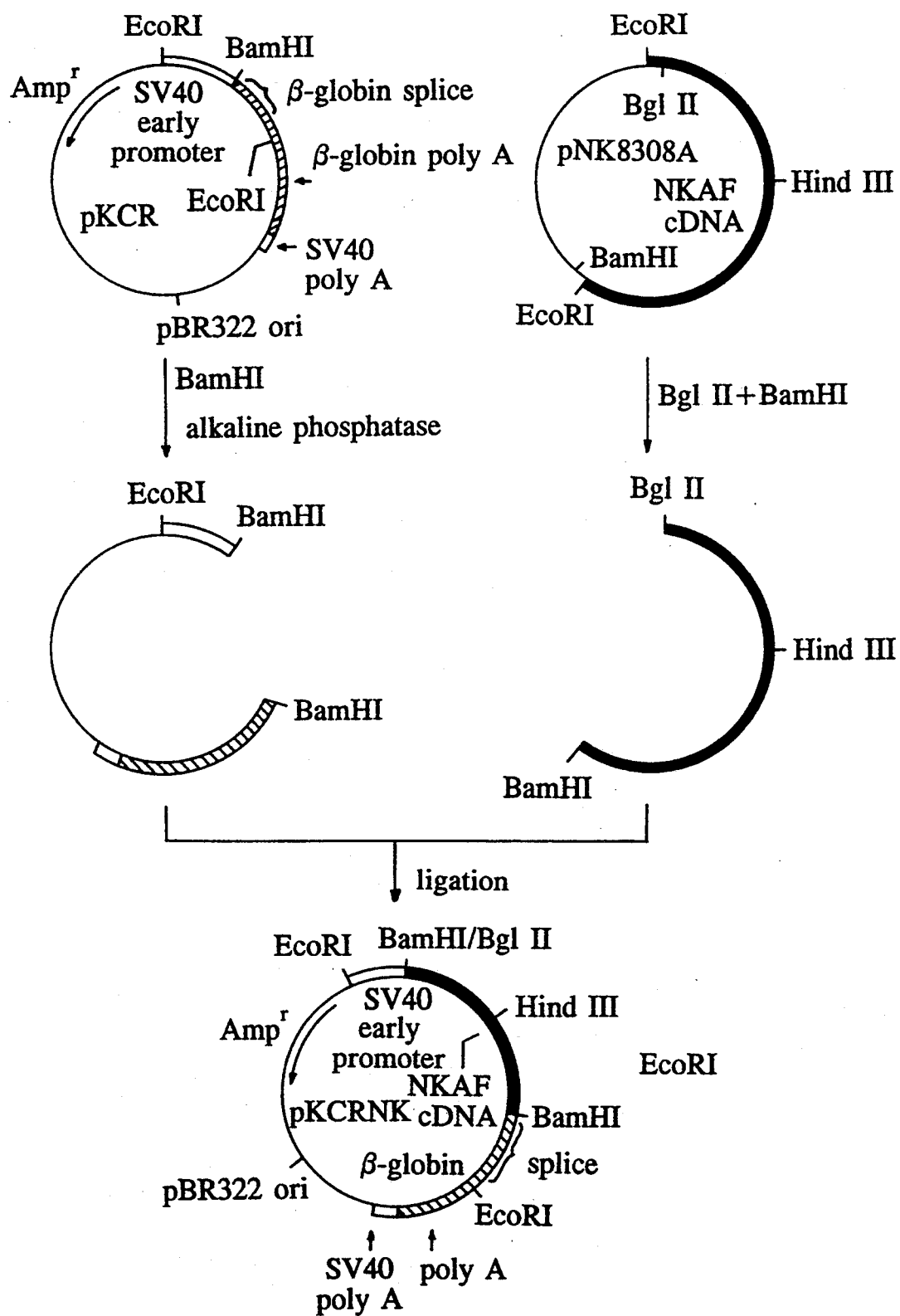
FIG. 1 is a figure showing a process for constructing pKCRNK.

To further illustrate the present invention in detail and concretely the following Examples will be given, though it is to be understood here that the present invention is never restricted thereto.

Example 1

Cloning of DNA sequence coding for AT III

By the use of a commercially available human liver cDNA library (λgt 11, available from Clonetech) as a starting material, screening was effected by a conventional method with a $^{32}$P-labeled synthetic oligonucleotide as a probe. The sequence of the synthetic oligonucleotide comprised the nucleotide sequence corresponding to the amino acids at the 314- to 322-positions of AT III based on the report by Chandra et al.

As the result of the screening two clones #2 and #6 were obtained. DNA fragments were collected from each clone by using a restriction enzyme EcoR I and subcloned into M13mp18 to thereby determine the nucleotide sequence. As a result, it was confirmed that the clone #2 contained a fragment of about 1.3 kb corresponding to the sequence of the 33rd amino acid to polyA, while another clone #6 contained a fragment of about 1.1 kb corresponding to the initiation codon to the 348th amino acid. Subsequently, inserts were excised from these clones by using EcoR I and each of the inserts was subcloned into pUC18 cleaved with EcoR I. Thus pUC-H and pUC-L were prepared respectively from the clones #2 and #6.

Next, a DNA fragment of about 3.7 kb (containing a sequence of about 1.0 kb corresponding to pUC18 and the N-terminal side of antithrombin III), which was obtained by cleaving pUC-L with Nco I and Hind III, was connected to another DNA fragment of about 0.5 kb (containing a sequence corresponding to the C-terminal side of antithrombin III) which was obtained by cleaving pUC-H with Nco I and Hind III. Thus a plasmid AT III FLpUC containing all coding regions ranging from the initiation codon to the terminator codon of AT III was obtained. The whole sequence from the initiation codon to tile terminator codon of the AT III cDNA contained in this plasmid was represented by SEQ ID No. 1 in the sequence listing.

Example 2

Insertion of restriction site

By the use of the plasmid AT III FLpUC obtained in the above Example 1 as a starting material, a DNA having a Hind III restriction site inserted immediately before the AT III coding sequence and a Bgl II restriction site immediately thereafter was prepared. First, AT III FLpUC was cleaved with EcoR I to thereby give a fragment of about 1.5 kb containing the whole AT III coding region. This fragment was inserted into the above-mentioned one obtained by cleaving RF of M13tv18 with EcoR I to linearize. Among the clones thus obtained, a clone giving the sense strand of AT III as a single-stranded DNA was referred to as tvATR. By using the single-stranded DNA of this tvATR as a template and the two synthetic oligonucleotides given below, each containing the restriction site of each enzyme, as a primer, the restriction sites were introduced in accordance with the method of Kramer et al.

AT5H 25mer

5′ TACATGGCCGAAGCTTCGTAATCAT (SEQ ID No:3)

AT3B 29mer

5'
CAAAGAATAAGATCTTATTACT-
TAACACA 3'                                    (SEQ ID No:4)

In the practical operation, a commercially available kit (Mutan G, manufactured by Takara Shuzo Co., Ltd.) was used. Namely, about 0.5 µg of the single-stranded DNA of tvATR and 0.2 µg of dsDNA contained in the kit (obtained by cleaving the RF DNA of a phage M13mpP lacking in a Pvu II fragment containing the multiple-cloning site of M13mp18 with Pvu II to linearize) were allowed to stand in 20 mM Tris.HCl pH 8-10 mM MgCl$_2$-50 mM NaCl-1 mM DTT at 100° C. for 3 minutes, at 65° C. for 10 minutes and at 37° C. for 10 minutes to thereby form a gapped duplex. A 1/10 portion of this gapped duplex was collected and mixed with 5 pmol portions of AT5H and AT3B the 5'-end of which had been substituted with phosphate with T4 polynucleotide kinase, and the resulting mixture (3 µl in total) was allowed to stand at 65° C. for 15 minutes and at 37° C. for 15 minutes. Next, 25 µl of a buffer solution contained in the kit [50 mM Tris-HCl pH 8-60 mM ammonium acetate - 5 mM MgCl$_2$-5 mM DTT-1 mM NAD-0.5 mM each of dNTPs (A, C, G, T)], 60 U of $E.$ $coli$ DNA ligase and 1 U of T4 DNA polymerase were added thereto and the resulting mixture was allowed to stand at 25° C. for about 2 hours. After adding 3 µl of 0.2 M EDTA (pH 8) and heating at 65° C. for 5 minutes, part of the mixture was collected and transfected into competent cells of an $E.$ $coli$ BMH71-18 mutS strain prepared by the method of Hanahan [see Hanahan, D., J. Mol. Biol., 166, 557 (1983)]. Plaques obtained by using an $E.$ $coli$ MV11184 strain as an indicator were picked and incubated by a conventional method to thereby give an RF DNA. This DNA was cleaved with restriction enzymes Hind III and Bgl II and the nucleotide sequence of a clone having a new restriction site was determined by the dideoxy method. Thus it was confirmed that the desired mutation had been introduced. The clone thus obtained was referred to as AT5H3B.

A DNA fragment of about 1.5 kb obtained by cleaving this AT5H3B with Hind III and EcoR I was inserted into M13tv19RF which had been subjected to linearize by similarly cleaving with Hind III and EcoR I. The clone thus obtained was referred to as tv19-5H3B. A DNA fragment obtained by cleaving a plasmid pSV2-dhfr [see Lee, F. et al., Nature, 294, 228 (1981); Subramani, S. et al., Mol. Cell. Biol., 1, 854 (1981)] with Hind III and Bgl II and eliminating a region coding for mouse dihydrofolate reductase (dhfr) was connected to another DNA fragment obtained by cleaving AT5H3B with Hind III and Bgl II too and containing the whole AT III coding region. Thus a plasmid pSV2-5H3B was obtained. Further, a DNA fragment of about 730 bp obtained by cleaving pSV2-5H3B with Hind III and Sac I and coding for the N-terminal side of AT III was inserted into M13tv19 and M13mp19 which had been subjected to linearize by cleaving with Hind III and Sac I to thereby respectively give tv19-ATN and mp19-ATN.

Example 3 a) Preparation of 1R mutant DNA

A sequence coding for an AT III mutant 1R wherein the 392nd Gly of AT III had been substituted with Pro (Table 3) was obtained by the site-directed mutagenesis method. Namely, in accordance with the method of Kramer et al., the single-stranded DNA of AT5H3B obtained in Example 2 was used as a template and treated with a synthetic oligonucleotide AT1R (Table 1) to thereby give the desired clone 1Rmut. The operation was effected by using a commercially available kit (Mutan G) by the same method as the one described in Example 2.

Twelve plaques thus obtained were picked up and analyzed. As a result, five of these clones were found to be the desired ones. The RF DNA of the obtained clone was cleaved with Hind III and Bgl II and the DNA fragment of about 1.4 kb thus obtained was replaced with a mouse DHFR gene in a plasmid pSV2-dhfr, similar to the procedure employed in Example 2, to thereby construct a plasmid pSV2-1R.

b) Preparation of other DNAs having mutation in the neighborhood of the reactive site In order to introduce a mutation in the neighborhood of the reactive site other then 1R, the above-mentioned method of Kramer et al. was effected by using tV19-5H3B obtained in Example 2 as a template. Thus substitutions of 5R, 26R, 28R, 29R, 30R, 39R, 40R, 46R, 48R, 49R, 50R, 27R, 7R, 34R, 35R, 38R, 9R, 19R, 24R, 2R', 5R' and 6R' were introduced. The amino acid sequence in the neighborhood of the reactive site of each of these AT III mutants is given in Table 3, while the sequences of synthetic oligonucleotides employed for the introduction of the mutations are listed in Tables 1 and 2. Similar to the procedure described in Example 2, a reaction for introducing a substitution was performed in accordance with the manual accompanying the kit and several clones thus formed were collected. Then the nucleotide sequences were determined and thus the clones having the desired substitution introduced thereinto were obtained. From each clone, a DNA fragment of about 1.4 kb was obtained by using Hind III and Bgl II. In the cases of 5R, 26R, 28R, 30R, 27R, 7R, 19R, 24R, 2R', 5R' and 6R', the obtained fragments were replaced with a mouse DHFR gene in pSV2-dhfr in the same manner as those described in Example 2 and Example 3 a) to thereby respectively give plasmids pSV2-5R, pSV2-26R, pSV2-28R, pSV2-30R, pSV2-27R, pSV2-7R, pSV2-19R, pSV2-24R, pSV2-2R', pSV2-5R' and pSV2-6R'. In the cases of 39R, 40R, 46R, 48R, 49R, 50R, 34R, 35R and 38R, on the other hand, each of the DNA fragments was replaced with a part of an NKAF gene in a plasmid pK4K which will be described hereinbelow to thereby respectively give plasmids pK4K-39R, pK4K-40R, pK4K-46R, pK4K-48R, pK4K-49R, pK4K-50R, pK4K-34R, pK4K-35R and pK4K-38R. In the cases of 29R and 9R, DNA fragments of about 1.4 kb were isolated again from plasmids pSV2-29R and pSV2-9R by using Hind III and Bgl II and plasmids pK4K-29R and pK4K-9R were constructed by the same method as those described above.

Example 4

Preparation of heparin binding site-mutated DNA

Among substitutions at the heparin binding site, the mutations of 1G, 2G and 8G were introduced in accordance with the method of Kramer et al. by using tv19-5H3B obtained in Example 2 as a template. The sequences of synthetic oligonucleotides employed therein are given in Table 2. The clones having the desired substitution introduced thereinto were referred to as 1Gmut, 2Gmut and 8Gmut respectively. From these clones, DNA fragments off about 1.4 kb were excised by using Hind III and Bgl II and treated by the same method as the one employed in the cases of the mutations at the reactive site. Thus plasmids pSV2-1G, pSV2-2G and pSV2-8G were obtained. Further, a DNA fragment of about 730 bp obtained by cleaving pSV2-1G with Hind III and Sac I was inserted into M13tv19 cleaved with the same enzymes to thereby give tv19-1GN.

The mutations of 1F, 2F, 3F and 7G were introduced in the same manner by using tv19-ATN obtained in Example 2 as a template. The M13 clones having the desired substitution introduced thereinto were referred to as 1Fmut, 2Fmut, 3Fmut and 7Gmut, respectively.

The mutation of 9G was introduced in accordance with the method of Vandeyar et al. with the use of mp19-ATN as a template. The practical operation was performed in accordance with the manual accompanying a kit (T7-GEN In Vitro Mutagenesis System available from USB). First, 1 μg of mp19-ATN single-stranded DNA and 2 pmol of a synthetic oligonucleotide AT9G, the 5'-end of which had been substituted with phosphate with T4 polynucleotide kinase, were heated at 65° C. in 40 mM Tris-HCl pH 7.5–20 mM $MgCl_2$-50 mM NaCl for 5 minutes and then slowly cooled to room temperature. To this reaction mixture (10 μl) were added 2 μl of 10 X Synthesis mix (100 mM Tris-HCl pH 7.5–20 mM DTT -5 mM dATP-5 mM dGTP-5 mM dTTP -5 mM 5-methyl-dCTP -10 mM ATP), 2.5 U of T7 DNA polymerase and 5 U of T4 DNA ligase to thereby give a final volume of 20 μl, followed by allowing to stand at 37° C. for 1 hour. Thus an RF DNA, in which the strand having a mutation introduced thereinto had exclusively methylated, was synthesized. After inactivating the enzyme by heating the reaction mixture at 70° C. for 10 minutes, 5 U portions of restriction enzymes Msp I and Hha I were added and allowed to react at 37° C. for 45 minutes. Thus one of the DNA strands of the double-stranded DNA used as a template which had not been methylated was exclusively nicked with Msp I and the template single-stranded DNA which had not been replicated into the double-stranded one was cleaved with Hha I. Subsequently, 50 U of exonuclease III was added to the reaction mixture and allowed to react at 37° C. for 45 minutes. Then only the nicked template strand was digested and, as a result, the DNA strand having mutation introduced thereinto was concentrated. After ceasing the reaction by heating at 70° C. for 10 minutes, the reaction mixture was transfected into an *E. coli* SDM strain (mcrAB) free from any restriction system specific for methylated DNA by an ordinary method. Several plaques thus obtained were picked up and DNAs were obtained. Then the nucleotide sequences thereof were determined and thus a clone having the desired substitution introduced thereinto was selected. From the clone thus obtained, a DNA fragment of about 730 bp was isolated by using Hind III and Sac I and inserted into pSV2-5H3B which had been cleaved with the same enzymes to thereby eliminate fragments of the same size. Thus pSV2-9G was obtained.

The 12G mutant was obtained by further introducing a substitution by using a synthetic oligonucleotide AT2G (Table 2) with the use of a DNA having the substitution of 1G introduced thereinto as a template. Namely, it was obtained in accordance with the method of Kramer et al. by using tv19-1GN as a template. After confirming that the desired mutation had been introduced, the obtained clone was referred to as 12Gmut.

The 127G mutant was obtained in accordance with the above-mentioned method of Vandeyar et al. by using a single-stranded DNA of 12Gmut as a template and treating with a synthetic oligonucleotide AT7G. After confirming that the desired substitution had been introduced, the obtained clone was referred to as 27Gmut.

Example 5

Preparation of DNA having substitutions both in the neighborhood of the reactive site and at the heparin binding site a) Preparation of 1G5R mutant DNA A DNA of the 1G5R mutant having a combination of a mutation 1G at the heparin binding site with another mutation 5R in the neighborhood of the reactive site was constructed in the following manner.

The RF DNA of 1Gmut obtained in Example 4 was cleaved with Hind III and Sac I and thus a DNA fragment of about 730 bp having a mutation at the heparin binding site was prepared. The pSV2-5R obtained in Example 3 was cleaved with Sac I and Bgl II and thus a DNA fragment of about 670 bp having a mutation in the neighborhood of the reactive site was prepared. These DNA fragments were combined together and inserted into pSV2-dhfr from which a mouse DHFR gene had been eliminated by using Hind III and Bgl II. Thus pSV2-1G5R was constructed. Further, this pSV2-1G5R was cleaved with Hind III and Bgl II and a DNA fragment of about 1.4 kb thus formed was inserted into a plasmid which was obtained by eliminating a part of a NKAF gene in a plasmid pK4K as will be described hereinafter by cleaving the plasmid pK4K with Hind III and BamH I. Thus pK4K-1G5R was constructed. The preparation of these DNA fragments having mutation and the construction of pSVS-1G5R and pK4K-1G5R by combining these mutated DNA fragments were performed in accordance with publicly known methods. *E. coli* HB101-pK4K-1G5R containing the plasmid pK4K-1G5R has been deposited with Fermentation Research Institute of Agency of Industrial Science and Technology of the Ministry of International Trade and Industry under the accession number of FERM BP-3806, on Mar. 26, 1992.

b) Preparation of 2G5R mutant DNA

A DNA of the 2G5R mutant having a combination of a mutation 2G at the heparin binding site with another mutation 5R in the neighborhood of the reactive site was constructed in the following manner.

The RF DNA of 2Gmut obtained in Example 4 was cleaved with Hind III and Sac I and thus a DNA fragment of about 730 bp having a mutation at the heparin binding site was prepared. The pSV2-5R obtained in Example 3 was cleaved with Sac I and Bgl II and thus a DNA fragment of about 670 bp having a mutation in the neighborhood of the reactive site was prepared. These DNA fragments were combined together and inserted into pSV2-dhfr from which a mouse DHFR gene had been eliminated by using Hind III and Bgl II. Thus pSV2-2G5R was constructed. Further, this pSV2-2G5R was cleaved with Hind III and Bgl II and a DNA fragment of about 1.4 kb thus formed was inserted into a plasmid which was obtained by eliminating a part of a NKAF gene in a plasmid pK4K as will be described hereinafter by cleaving the plasmid pK4K with Hind III and BamH I. Thus pK4K-2G5R was constructed. *E. coli* HB101-pK4K-2G5R containing the plasmid pK4K-2G5R has been deposited with Fermentation Research Institute of Agency of Industrial Science and Technology of the Ministry of International Trade and Industry under accession number of FERN BP-3807, on Mar. 26, 1992.

c) Preparation of other both site-mutated DNAs

The DNAs each having a mutation at the corresponding site obtained in Examples 3 and 4 were employed. As a DNA fragment having a mutation at the heparin binding site, DNA fragments of about 730 bp obtained by cleaving pSV2-1G, pSV2-2G, pSV2-9G, 1Fmut, 2Fmut, 3Fmut. 7Gmut, 12Gmut and 127 Gmut each with Hind III and Sac I were prepared. Separately, as a DNA fragment having a substitution at the reactive site, DNA fragments of about 670 bp were obtained by cleaving pSV2-1R, pSV2-5R (or pSV2-1G5R) and pSV2-30R each with Sac I and Bgl II. Further, pK4K-35R was cleaved with Sac I and Xho II to thereby give a DNA fragment of about 670 bp (In a DNA prepared by inserting an AT III mutant gene with a Hind III-Bgl II fragment into a plasmid wherein a part of an NKAF gene had been eliminated from pK4K by cleaving with Hind III and BamH I, the Bgl II-cleaved end is connected to the BamH I-cleaved end. Thus it is impossible to cleave this DNA again with Bgl II. However, this site can be cleaved with Xho II.). These DNA fragments were combined together and then inserted into a plasmid wherein a part of the NKAF gene had been eliminated from pK4K by cleaving with Hind III and BamH I. Thus pK4K-1G30R, pK4K-1G35R, pK4K-2G30R, pK4K-2G35R, pK4K-1F5R, pK4K-2F5R, pK4K-3F5R, pK4K-7G5R, pK4K-7G30R, pK4K-7G35R, pK4K-9G5R, pK4K-9G30R, pK4K-9G35R, pK4K-12G5R, pK4K-12G30R, pK4K-12G35R, pK4K-127G5R, pK4K-127G30R and pK4K-127G35R were constructed. Furthermore, pSV2-1G1R and pSV2-2G1R were constructed in a similar manner by using pSV2-dhfr from which a mouse DttFR gene had been eliminated with the use of Hind III and Bgl II.

Example 6

Construction of expression vector for animal cells a) Construction of natural recombinant AT III and 1R expression vector A plasmid pNK8308 (disclosed in European Patent Publication-A3 No. 357067) containing a cDNA coding for recombinant natural killer cell activating factor (NKAF) was digested with Bgl II and BamH I and electrophoresed on an agarose gel. Thus an NKAF cDNA fragment of about 0.75 kb was isolated. A plasmid pKCR [see 0 Hare, K. et al., Proc. Natl. Acad. Sci. USA, 78, 1527 (1981)] was digested with BamH I and dephosphorylated with alkaline phosphatase. The vector DNA thus obtained was connected (ligated) to the NKAF cDNA fragment by adding T4 DNA ligase to thereby give pKCRNK (FIG. 1).

Figure 2:
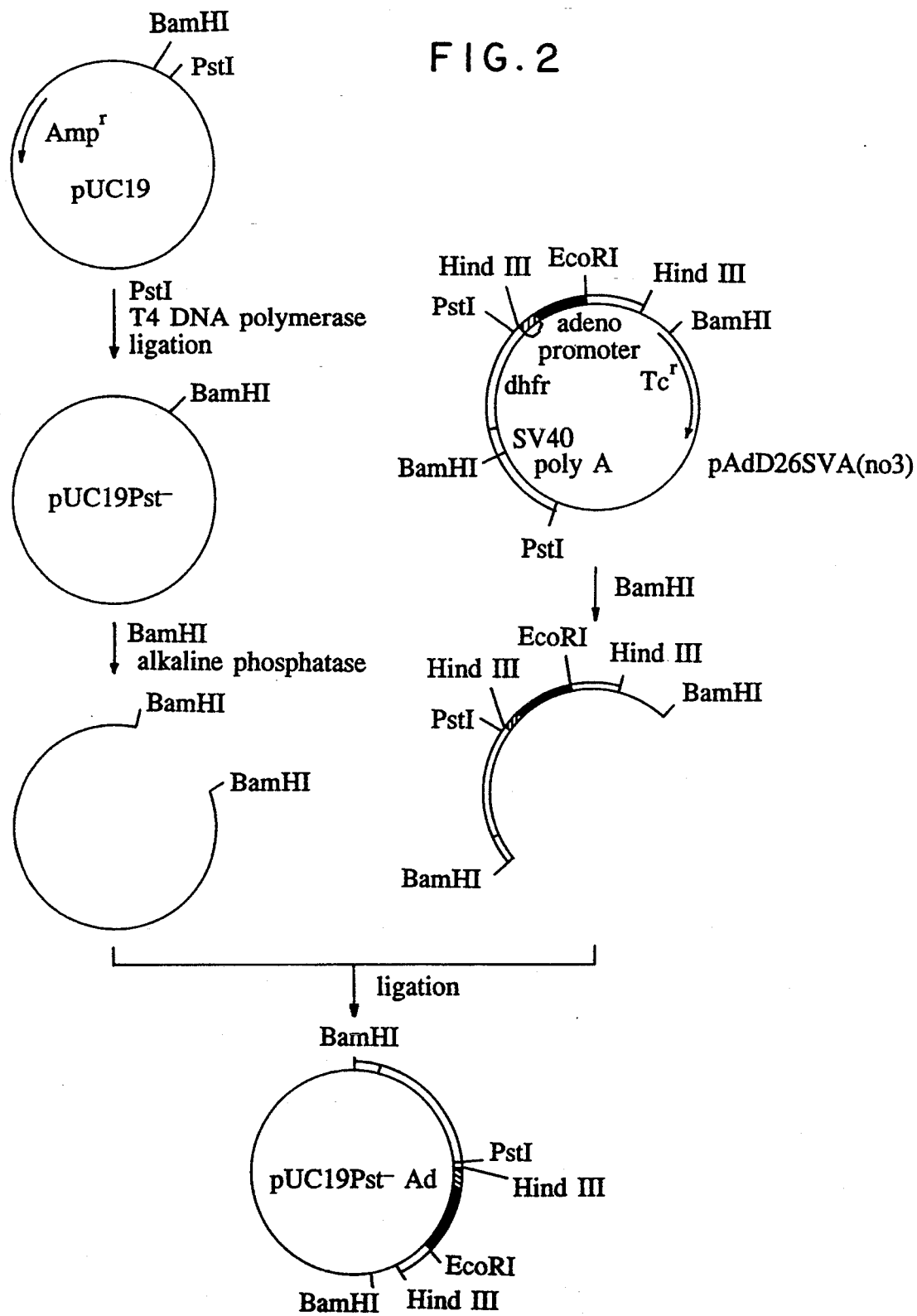
FIG. 2 is a figure showing a process for constructing pUC19st⁻Ad.
Figure 3:
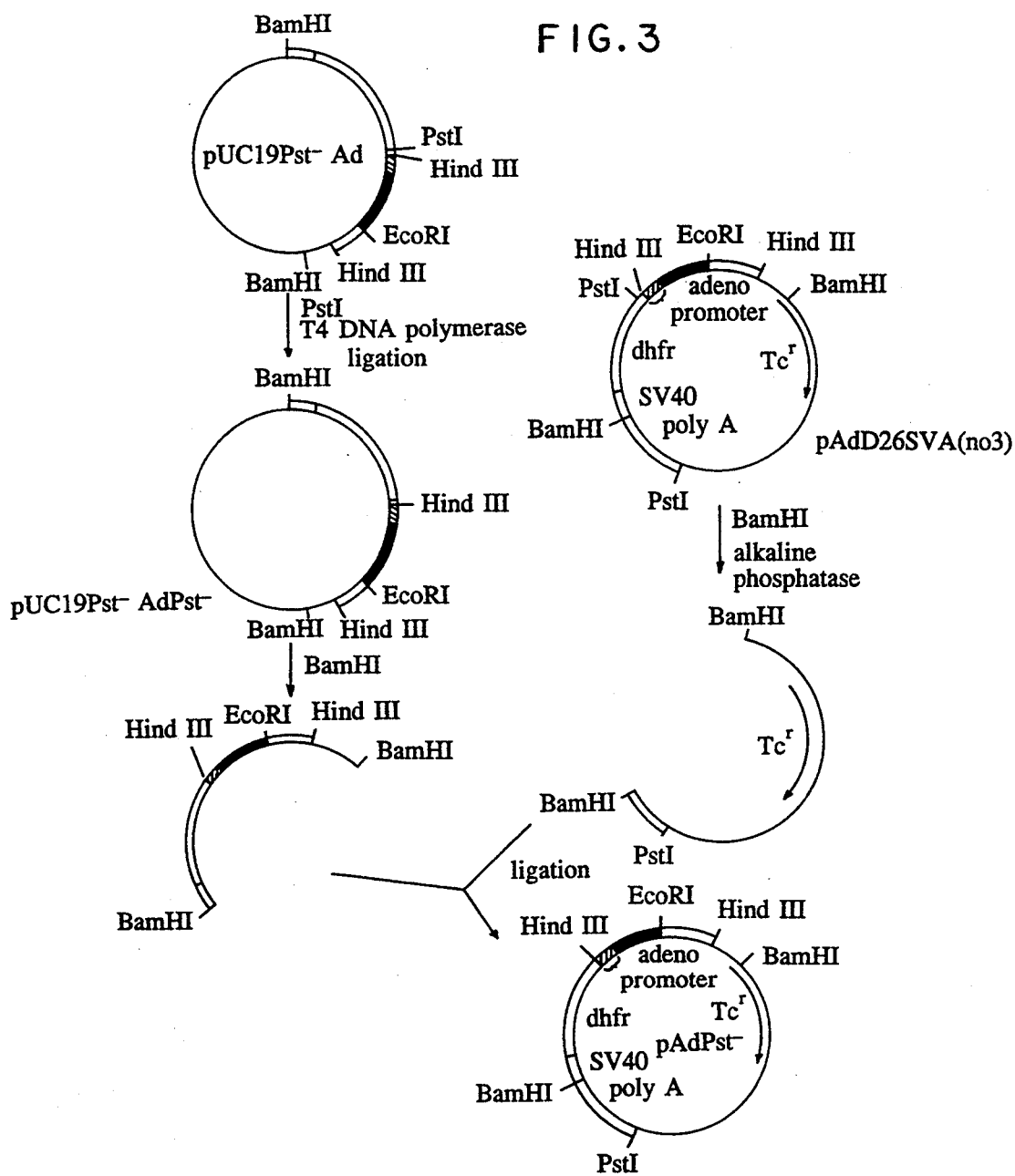
FIG. 3 is a figure showing a process for constructing pAdPst⁻.
Figure 4:
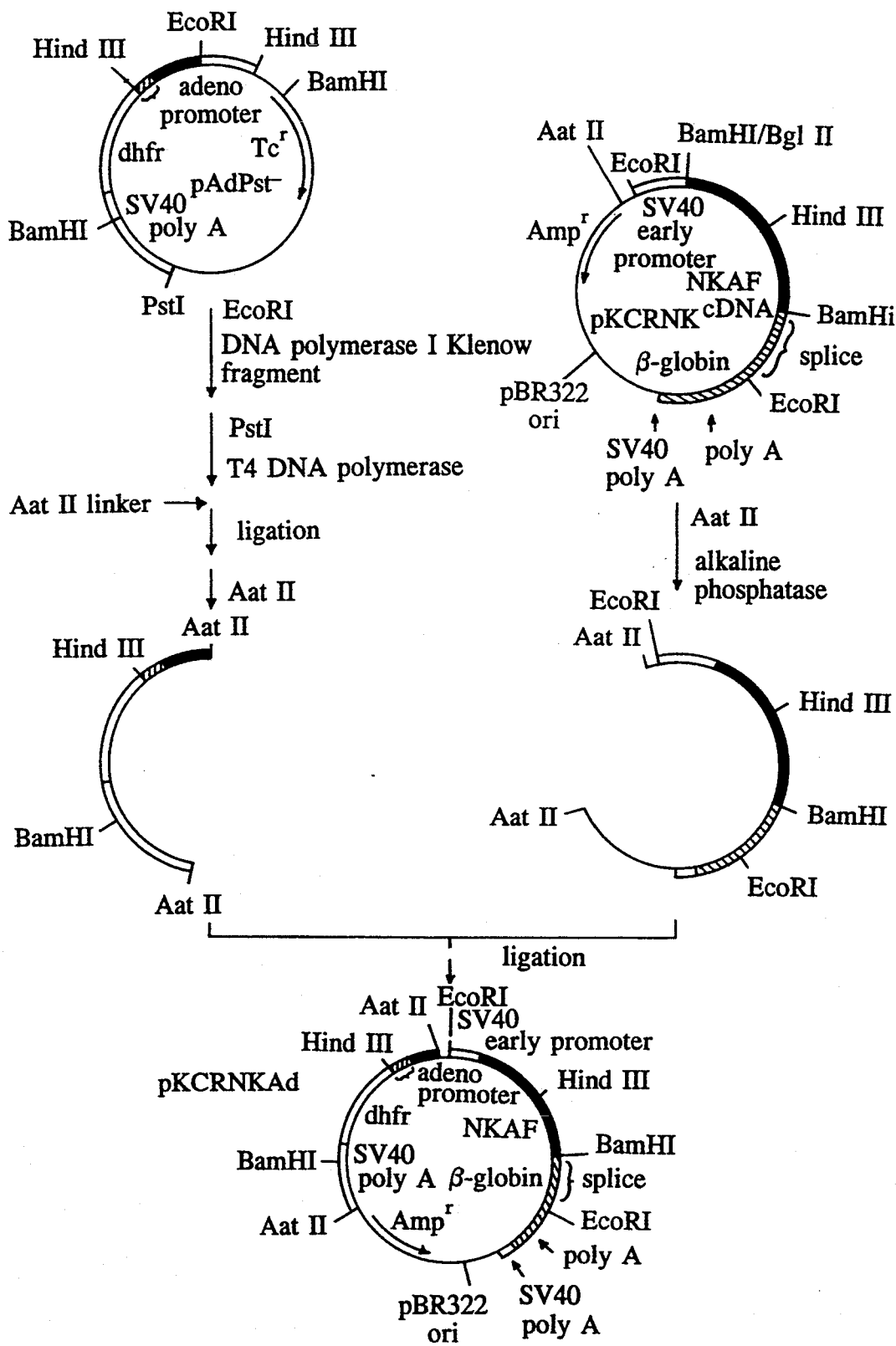
FIG. 4 is a figure showing a process for constructing pKCRNKAd.

A plasmid pUC19 was digested with Pst I, then treated with T4 DNA polymerase by a conventional method to thereby blunt (to thereby be blunt-ended) both of the 3'- and 5'-ends and then ligated, thus giving pUC19Pst−. Subsequently, this pUC19Pst− was digested with BamH I and dephosphorylated with alkaline phosphatase. The vector DNA thus obtained was ligated with a DNA fragment of about 2.4 kb [containing adenovirus promoter, mouse dihydrofolate reductase (DHFR) gene and SV40 polyA signal], which had been isolated by digesting a plasmid pAdD26SV(A) (no.3) [see Kaufmann, R. and Sharp, P., Mol. Cell. Biol., 2 1304 (1982)] with BamH I and electrophoresing on an agarose gel, to thereby give pUC19Pst− Ad (FIG. 2). Further, this pUC19Pst− Ad was digested with Pst I and blunt-ended with T4 DNA polymerase and then ligated to thereby give pUC19Pst− AsPst−. Then a DNA fragment of about 2.9 kb containing a tetracycline-resistant gene, which had been isolated by digesting pAdD26SV(A) (no. 3) with BamH I, dephosphorylating and electrophoresing on an agarose gel, was ligated with another DNA fragment of about 2.4 kb containing adenovirus promoter, mouse DHFR gene and SV40 polyA signal, which had been isolated by digesting pUC19Pst− AdPst− with BamtI I and electrophoresing on an agarose gel, to thereby give pAdPst− (FIG. 3). Then the pAdPst− was digested with EcoR I and blunt-ended by treating with a DNA polymerase I Klenow fragment. Subsequently, it was digested with Pst I and blunt-ended with T4 DNA polymerase. Then Aat II linker was added thereto and ligated therewith and the obtained product was digested with Aat II and electrophoresed on an agarose gel. Thus a DNA fragment of about 2.7 kb containing adenovirus promoter, mouse DHFR gene and SV40 polyA signal was obtained. This DNA fragment was ligated with a DNA obtained by digesting pKCRNK with Aat II and dephosphorylating to thereby give pKCRNKAd (FIG. 4).

Figure 5:
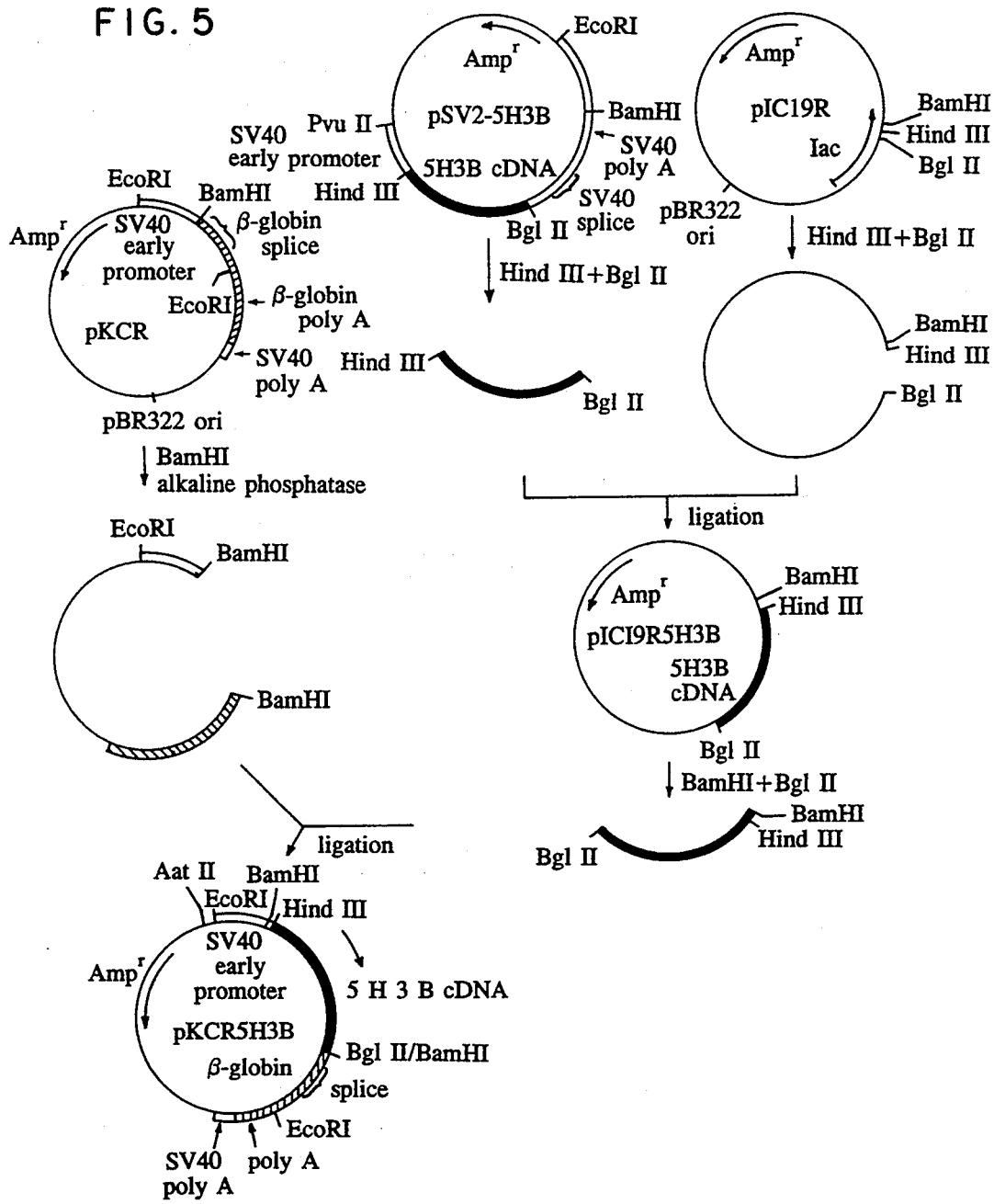
FIG. 5 is a figure showing a process for constructing pKCR5H3B.
Figure 6:
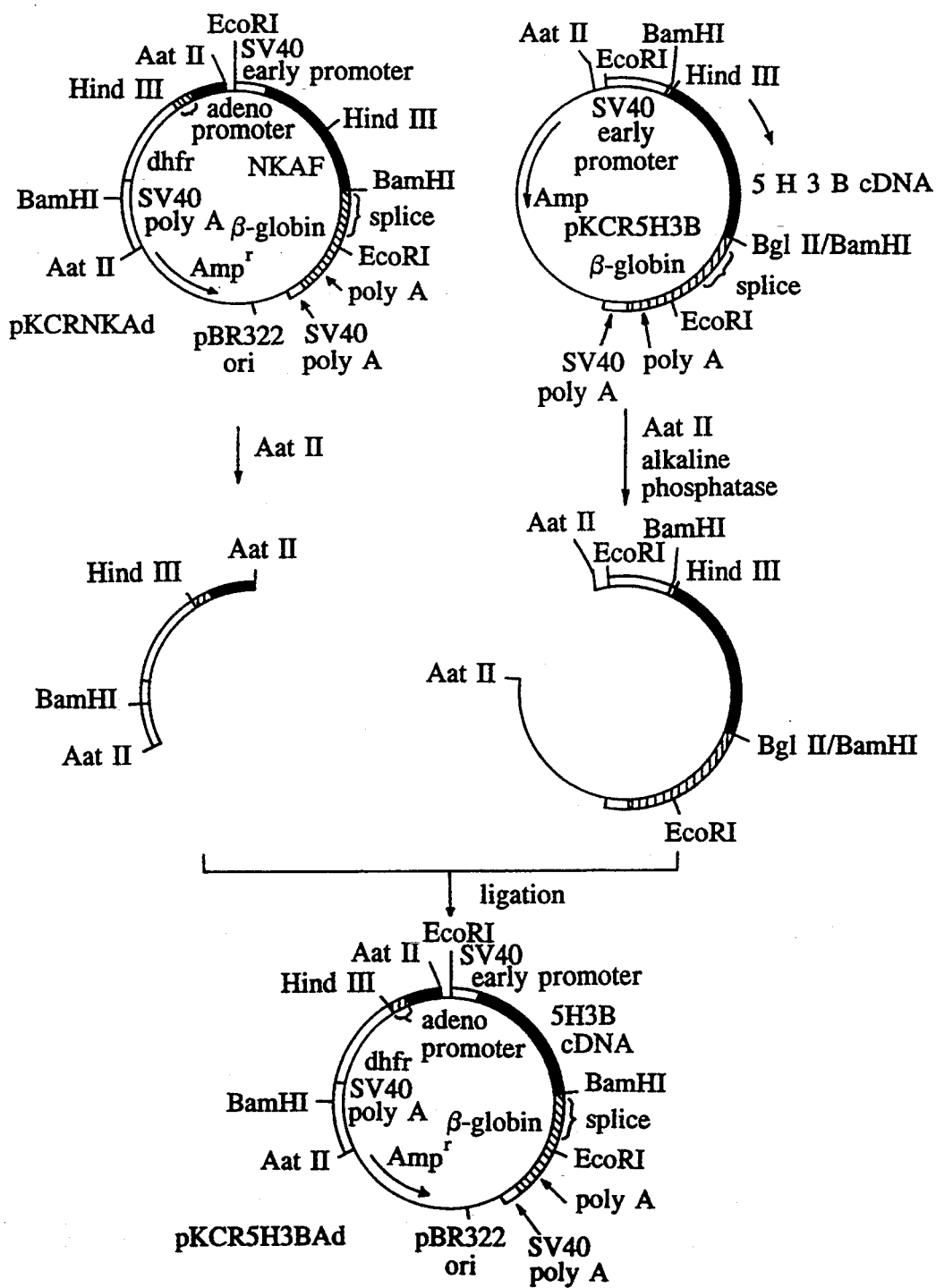
FIG. 6 is a figure showing a process for constructing pKCR5H3BAd.

The plasmid pSV2-5H3B obtained in Example 2 was digested with Hind III and Bgl II and a DNA fragment of about 1.4 kb containing AT III cDNA was isolated. This fragment was lligated with a vector DNA obtained by digesting a plasmid pIC19R [see Marsh, J. L. et. al., Gene, 32, 481 (1984)]with Hind III and Bgl II to thereby give pIC19R5H3B. Next, this pIC19R5H3B was digested with BamH I and Bgl II and a DNA fragment of about 1.4 kb containing 5H3B cDNA was isolated. This DNA fragment was ligated with a vector DNA obtained by digesting pKCR with BamH I and dephosphorylating to thereby give pKCR5H3B (FIG. 5).

pKCRNKAd was digested with Aat II and a DNA fragment of about 2.7 kb containing adenovirus promoter, mouse DHFR gene and SV40 polyA signal was isolated. This DNA fragment was ligated with a vector DNA obtained by digesting pKCR5H3B with Aat II and dephosphorylating to thereby give pKCR5H3BAd (FIG. 6). The pKCR5H3BAd was used in order to express a natural recombinant AT III in animal cells as will be described in Example 7.

Figure 7:
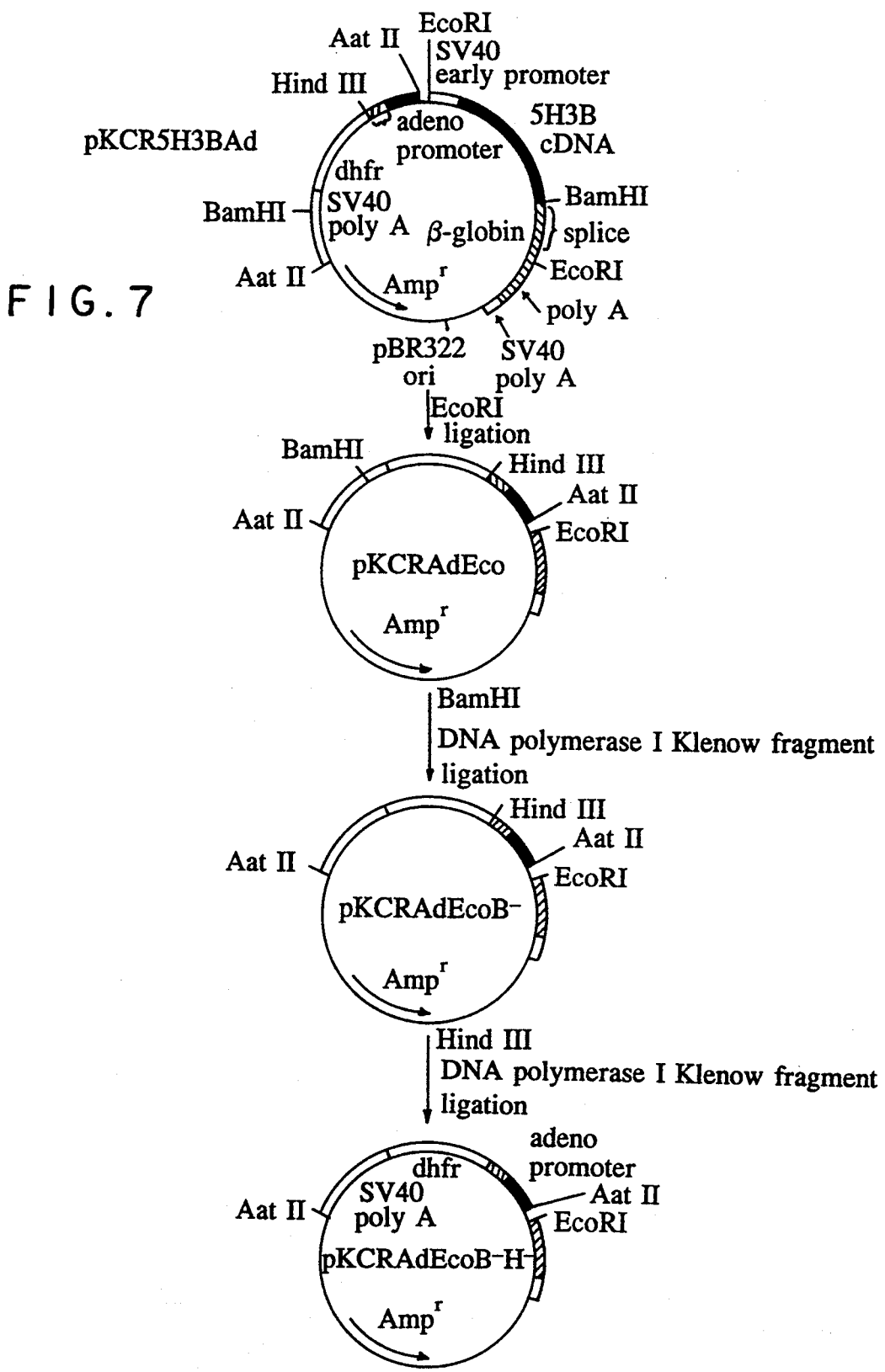
FIG. 7 is a figure showing a process for constructing pKCRAdEcoB⁻H⁻.
Figure 8:
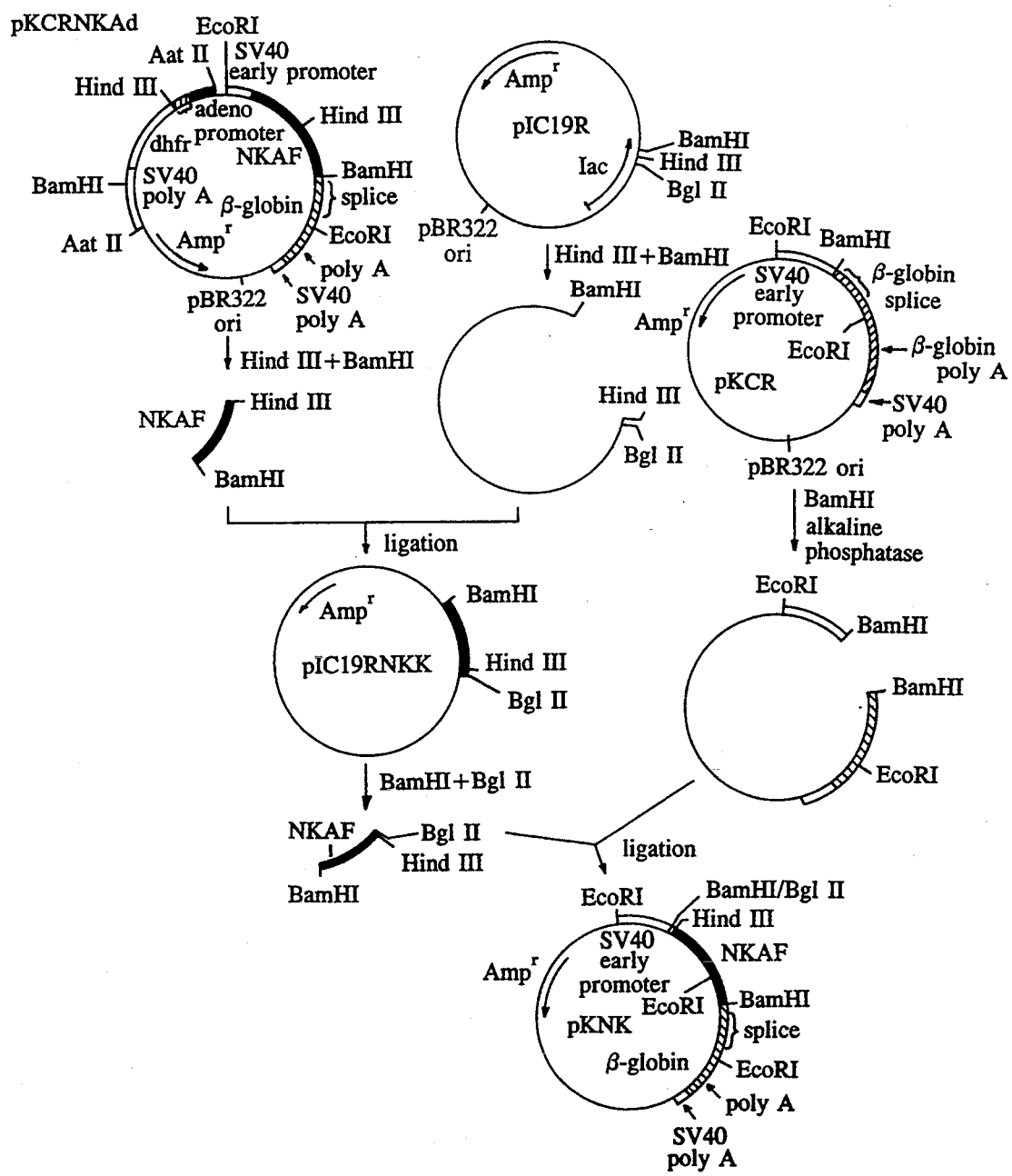
FIG. 8 is a figure showing a process for constructing pKNK.

Similarly, by the use of pSV2-1R obtained in Example 3 a) as the starting material, pKCR1RAd was obtained. The pKCR1RAd was used in order to express a mutant 1R in animal cells as will be described in Example 7.

b) Construction of expression vectors of various mutants in animal cells pKCR5H3BAd was digested with EcoR I and then self-ligated. Thus pKCRAdEco wherein SV40 promoter, a part of the NKAF gene and a part of rabbit β-globin gene had been eliminated was selected. The pKCRAdEco was digested with BamH I, blunt-ended with a DNA polymerase I Klenow fragment and then ligated to thereby give pKCRAdEcoB−. Subsequently, the pKCRAdEcoB− was digested with Hind III, blunt-ended with a DNA polymerase I Klenow fragment and then ligated to thereby give pKCRAdEcoB−H− (FIG. 7).

pKCRNKAd was digested with Hind III and BamH I and a DNA fragment of about 0.4 kb containing a part of the NKAF gene was isolated. Then it was ligated with a vector DNA obtained by digesting pIC19R with Hind III and Bamtt I to thereby give pIC19RNKK. The pIC19RNKK was digested with Bgl II and BamH I and a DNA fragment of 0.4 kb containing a part of the NKAF gene was isolated. This DNA fragment was ligated with a vector DNA obtained by digesting pKCR with BamH I and dephosphorylating to thereby give pKNK (FIG. 8).

pKNK was partially digested with EcoR I and a DNA fragment of about 1.5 kb containing SV40 promoter, a part of NKAF gene and a part of rabbit $\beta$-globin gene was isolated. Then this DNA fragment was ligated with a vector DNA obtained by digesting pKCRAdEcoB$^-$H$^-$ with EcoR I and dephosphorylating to thereby give pK4K (FIG. 9).

Figure 9:
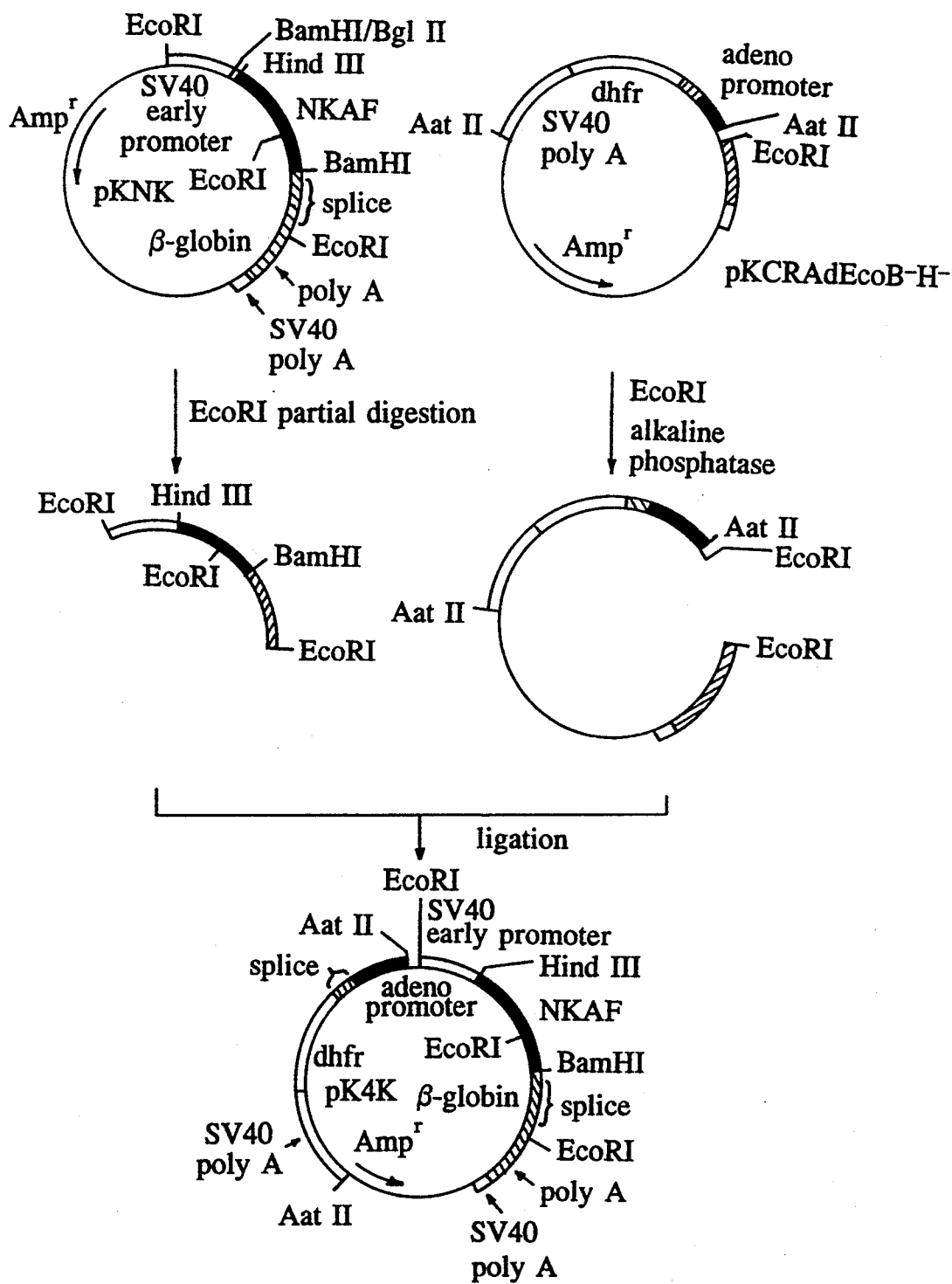
FIG. 9 is a figure showing a process for constructing pK4K.

As FIG. 9 shows, pK4K contains the promoter of an early gene of SV40, the replication initiation region of SV40, a part of the NKAF gene, a part of the rabbit $\beta$-globin gene (splicing and polyA signal), the polyA signal of the early gene of SV40, the major late gene promoter and the 5' splice signal of type II adenovirus, rabbit immunoglobulin 3' splice signal, mouse DHFR gene, the polyA signal of the early gene of SV40, the replication initiation region of pBR322 and a $\beta$-lactamase gene originating in pBR322 (Amp $\gamma$) and the dhfr was connected on the downstream side of the major late gene promoter of adenovirus and a part of the NKAF gene was connected on the downstream side of the promoter of the early gene of SV40.

An expression vector in animal cells can be constructed by inserting an AT III mutant gene into a site remaining after excising a part of the NKAF gene of pK4K with Hind III and BamH I. In practice, expression vectors of the mutants 1G5R and 2G5R were prepared by using pSV2-1G5R and pSV2-2G5R respectively and pK4K by the above-mentioned method as shown in Example 5 a) and b). These vectors were referred to as pK4K-1G5R and pK4K-2G5R. As described in Example 3 b) and Example 5 c), expression vectors of other mutants were similarly constructed by using pK4K.

c) Construction of expression vectors of mutants 5R and 7R

Figure 10:
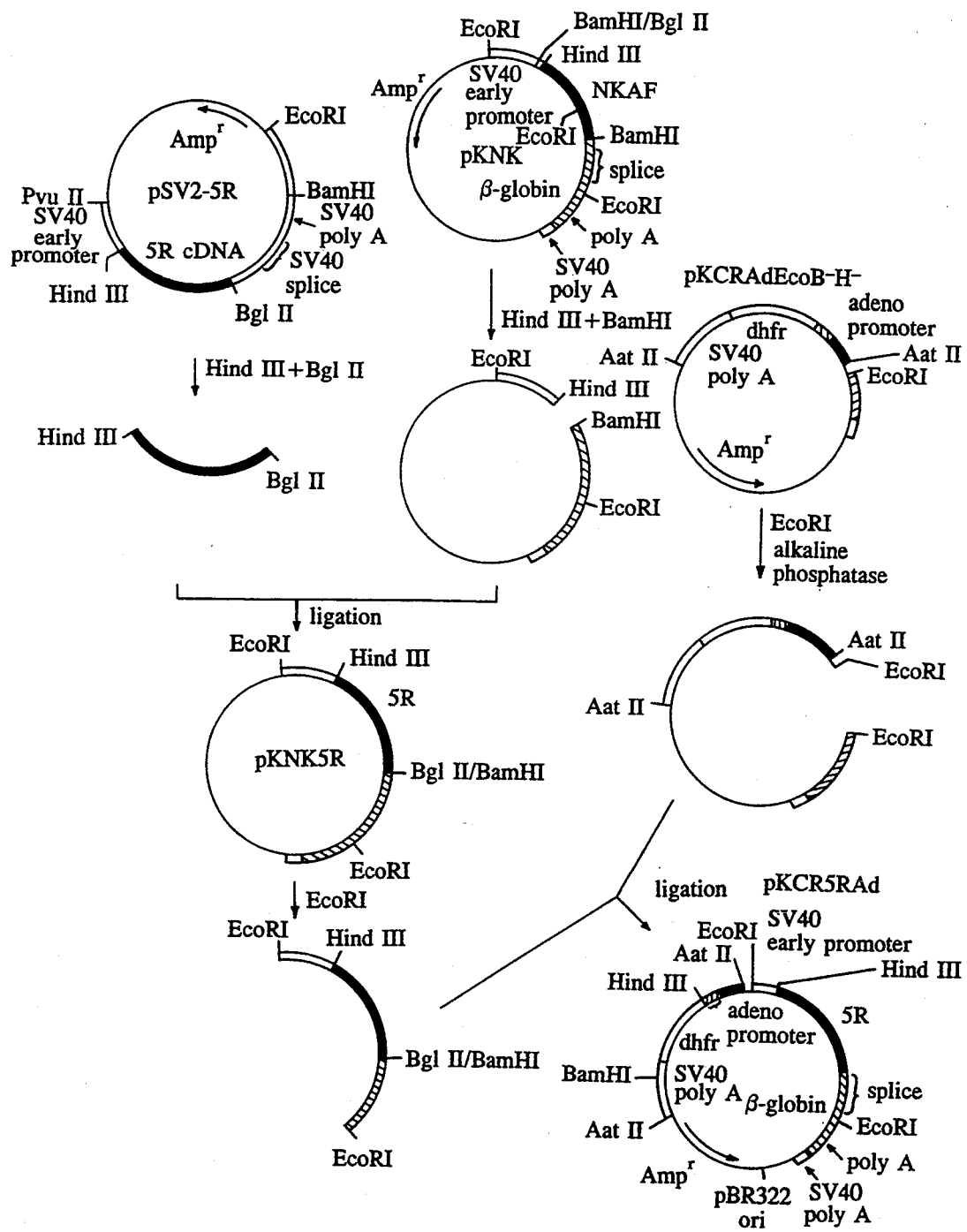
FIG. 10 is a figure showing a process for constructing pKCR5RAd.

The plasmid pSV2-5R obtained in Example 3 b) was digested with Hind III and Bgl II and thus a DNA fragment of about 1.4 kb containing a 5R gene was isolated. This DNA fragment was ligated with a vector DNA obtained by digesting pKNK with Hind III and BamH I to thereby eliminate a part of the NKAF gene, thus giving pKNK5R. The pKNK5R was digested with EcoR I and a DNA fragment of about 1.5 kb containing the promoter of the early gene of SV40, a 5R gene and a part of the rabbit $\beta$-globin gene was isolated. This DNA fragment was ligated with a vector DNA obtained by digesting pKCRAdEcoB$^-$H$^-$ with EcoR I and dephosphorylating to thereby give pKCR5RAd (FIG. 10). Similarly, pKCR7RAd was obtained by using pSV2-7R obtained in Example 3 b).

Example 7

Expression of AT III mutant by animal cells
a) Expression by CHO cell

CHO cells [dhfr-deficient strain, see Urlaub, G. and Chasin, L. A., Proc. Natl. Acad. Sci. USA, 77, 4216 (1980)] were inoculated in an incubation flask at a ratio of $7\times 10^5$ cells/5 ml/the flask of 25 cm$^2$. On the next day, 3 $\mu$g of the plasmid pKCR1RAd obtained in Example 6 a) was transfected by the calcium phosphate method with the use of a CellPhect (a kit manufactured by Pharmacia). As a medium, one obtained by adding fetal calf serum to a 1:1 mixture (a DF medium) of Ham F12 medium with Dulbecco's modified Eagle medium in such a manner that the obtained medium contained 10% of the fetal calf serum, was used. After 3 days, the cells were trypsinized and diluted with a selection medium (DF medium free from hypoxanthine and thymidine +10% dialyzed fetal calf serum). Then 1 ml portions of the cells contained in one incubation flask (25 cm$^2$) were pipetted into each of wells of four 24-well plates for incubation and the incubation was continued in the selection medium while replacing the medium with a fresh one at intervals of 3 to 4 days. Cells surviving under these conditions were those transformed by the mouse DHFR gene. After approximately 2 weeks, the colonies thus formed were dispersed by trypsinizing in wells and a fresh medium was added, followed by incubating for additional 3 to 4 days. Then the culture broth was exchanged and the amount of 1R contained in the culture supernatant was determined by the EIA method on the next day. Each clone showing an expression yield of about several ten ng/ml/day or more was transinoculated into a selection medium containing 50 nM of methotrexate (MTX) and incubated for 2 to 3 weeks. Further, the MTX concentration was successively elevated to 100 nM, 400 nM and 1000 nM and the incubation was continued in the same manner. Among clones growing at the MTX concentration of 1000 nM, those showing high expression yields were cloned by the limiting dilution method with the use of a 96-well plate. In the state of confluent growth, a clone 110-6, which was a typical example of those thus obtained, secreted about 10 $\mu$g/ml/day of 1R into the culture supernatant at 0.3 ml of the medium/cm$^2$. Similarly, CHO cells capable of expressing a natural recombinant AT III were obtained by using pKCR5H3BAd obtained in Example 6 a).

b) Expression of various mutants by BHK cell
i) Use of pSV2 vectors

The plasmids shown in Examples 3 and 5, which were constructed by replacing the mouse DHFR gene in a plasmid pSV2-dhfr by an AT III mutant DNA, can be used for expressing various mutants by transfecting into animal cells together with pSV2-dhfr (cotransfection).

BHK cells [tk$^-$ts13 strain, see Waechter, D. E. and Baserga, R., Proc. Natl. Acad. Sci. USA, 79, 1106 (1982)] were inoculated in an incubation flask at a ratio of $5\times 10^5$ cells/5 ml/the flask of 25 cm$^2$. On the next day, 7 $\mu$g of a plasmid pSV2-28R having a gene of a mutant 28R shown in Example 3 b) introduced thereinto was transfected into the BHK cells together with 3.5 $\mu$g of pSV2-dhfr by the calcium phosphate method with the use of CellPhect. As a medium, one obtained by adding fetal calf serum to Dulbecco's modified Eagle medium in such a manner that the obtained medium contained 5% of the fetal calf serum, was used. After 3 days, the cells were trypsinized and subcultured into a 75 cm$^2$ incubation flask with a medium containing 200 nM of MTX. After incubating for 10 days while replacing the medium with a fresh one at intervals of 2 to 5 days, the cells were subcultured into a 175 cm$^2$ incubation flask with a medium containing 1000 nM of MTX. After incubating for additional 10 days while replacing the medium with a fresh one at intervals of 2 to 3 days, a cell strain showing a high expression yield was cloned by the limiting dilution method with the use of a 96-well plate. A clone #4 thus obtained secreted about 0.7 $\mu$g/ml/day of 28R into tile culture supernatant at 0.3 ml of the medium/cm² in a state of confluent growth. Regarding the plasmids containing other mutant DNAs which were constructed with pSV2 and described in Examples 3 and 5, expression cells could be obtained by the same method as the one described above.

ii) Use of other vectors

BHK cells (tk⁻ts13 strain) were inoculated in an incubation flask at a ratio of $3\times10^5$ cells/5 ml/the flask of 25 cm². On the next day, 3 μg of a plasmid pK4K-2G5R having a gene of a mutant 2G5R obtained in Example 5 b) introduced thereinto was transfected into the BHK cells by the calcium phosphate method with the use of CellPhect. As a medium, one obtained by adding fetal calf serum to Dulbecco's modified Eagle medium in such a manner that the obtained medium contained 5% of the fetal calf serum, was used. After 2 days, the cells were trypsinized and diluted with a medium containing 250 nM of MTX. The cells in one 25 cm² incubation flask were pipetted into wells of twelve 24-well plates for incubation. Then the incubation was continued while replacing the medium with a fresh one at intervals of 3 to 4 days. After 12 days, the colonies thus formed were dispersed by trypsinizing in the wells and the medium was added. After incubating for additional 6 days, the culture broth was exchanged. On the next day, the amount of each mutant contained in the culture supernatant was measured by the EIA method and a cell strain showing a high expression yield was cloned. A clone 6-5 thus obtained secreted about 16 μg/ml/day of 2G5R into the culture supernatant at 0.3 ml of the medium/cm² in a state of confluent growth.

Regarding pKCR1RAd, pKCR5RAd and pKCR7RAd described in Example 6 and the plasmids containing other mutant DNAs described in Examples 3 and 5, which were constructed by using pK4K, expression cells were obtained in a similar manner. Further, cells capable of expressing the natural recombinant AT III could be obtained by the same method with the use of pKCR5H3BAd shown in Example 6.

Some of these expression cells were transinoculated into a medium containing 1000 nM of MTX and further incubated. Some of clones incubated in the medium containing 1000 nM of MTX, which showed high expression yields were cloned by the limiting dilution method with the use of a 96-well plate.

The expression yields of typical examples of the clones thus obtained were shown in Table 10.

TABLE 10

| | Expression of AT III mutant by BHK cell | | |
|---|---|---|---|
| Mutant | Clone | Amount of Secretion into medium (μg/ml) | MTX concn. (nM) |
| natural recombinant AT III | F242 | 15–20 | 1000 |
| 1R | 5–41 | 25–30 | 1000 |
| 5R | D153 | 13–15 | 1000 |

TABLE 10-continued

| | Expression of AT III mutant by BHK cell | | |
|---|---|---|---|
| Mutant | Clone | Amount of Secretion into medium (μg/ml) | MTX concn. (nM) |
| 7R | 3–153 | 20–25 | 1000 |
| 1G5R | 11–1 | 10 | 1000 |
| 6R' | 5–21 | 15 | 1000 |
| 30R | 6–18 | 19 | 1000 |
| 2G5R | 6–5 | 16 | 250 |
| 25R | 4–2 | 20 | 250 |
| 35R | 42–5 | 22 | 250 |
| 29R | 22–8 | 17 | 250 |
| 2G30R | 16 | 19 | 250 |
| 7G5R | 1 | 12 | 250 |

The amount of secretion into the medium was expressed in the mutant concentration 24 hours after replacing the medium in a state of confluent growth of cells (the amount of medium was 0.3 ml/cm2). Example 8

Incubation of mutant expression cells and purification of mutant

The AT III mutant expression cells obtained in Example 7 were incubated in a roller bottle (1750 cm2). As a medium, Dulbecco's modified Eagle medium containing 5% of fetal calf serum and MTX (final concentration being 250 nM or 1000 nM) was used. The cells were inoculated into 300 ml of the medium and incubated at 37° C. From 3 to 4 days after the initiation of the incubation, the medium was replaced by the same amount of a fresh one everyday and the culture supernatants were combined.

The AT III mutants were purified by affinity chromatography with the use of an antibody column wherein anti AT III monoclonal antibody was bound to a support. Namely, the above-mentioned culture supernatant was charged into an antibody column which had been equilibrated with 50 mM Tris-HCl buffer pH 7.5–0.5 M NaCl. After washing with the same buffer, it was eluted with 0.2 M glycine-HCl buffer (pH 2.5). The eluted fractions were immediately neutralized with ½ times by volume as much 1 M Tris-HCl (pH 8.0). The fractions thus obtained were dialyzed against Dulbecco's PBS (−), ultrafiltrated and then used in the subsequent test. In the cases of some mutants, the eluted fractions from the antibody column was ultrafiltrated, charged into Sepharcryl S-200 and eluted with Dulbecco's PBS (−) (gel-filtration). The active fraction thus obtained was concentrated and then used in the subsequent test.

During the process of incubation and purification, each AT III mutant was determined by the EIA method with the use of anti AT III antibody.

The natural recombinant AT III employed as a control was also incubated and purified by the same method.

What we claim is:

1. A human antithrombin III mutant exhibiting elevated antithrombin activity, said human antithrombin III mutant having the identical amino acid sequence as that of human antithrombin III except that one of the following mutations has occurred: Gly at the 392 position is substituted by Pro, Ala at the 384 position is substituted by Gly, Val at the 389 position is substituted by Pro, Ala at the 387 position is substituted by Phe, Asn at the 398 position is substituted by Glu, or Asn at the 398 position is substituted by Arg.

2. A human antithrombin III mutant exhibiting elevated antithrombin activity, said human antithrombin III mutant having the identical amino acid sequence as that of human antithrombin III except that the following mutation has occurred: Gly at the 392 position is substituted by Pro and Ala at the 391 position is substituted by a member selected from the group consisting of Phe, Ile, Gly, Tyr, Trp, Val and Leu.

3. A human antithrombin III mutant exhibiting elevated antithrombin activity, said human antithrombin III mutant having the identical amino acid sequence as that of human antithrombin III except that the following mutation has occurred: Ile at the 390 position is substituted by Ala and Ala at the 391 position is substituted by a member selected from the group consisting of Val, Ile and Leu or Ile at the 390 position is substituted by Gly and Ala at the 391 position is substituted by Leu.

4. A human antithrombin III mutant exhibiting elevated antithrombin activity, said human antithrombin III mutant having the identical amino acid sequence as that of human antithrombin III except that the following mutation has occurred: Lys at the 125 position is substituted by Gln, Ala at the 391 position is substituted by Phe and Gly at the 392 position is substituted by Pro or Lys at the 125 position is substituted by Gln and Gly at the 392 position is substituted by Pro.

5. A human antithrombin III mutant exhibiting elevated antithrombin activity, said human antithrombin III mutant having the identical amino acid sequence as that of human antithrombin III except that the following mutation has occurred: Ile at the 390 position is substituted by Ala, Ala at the 391 position is substituted by a member selected from the group consisting of Val, Tyr and Trp, and Gly at the 392 position is substituted by Pro or Ile at the 390 position is substituted by Leu, Ala at the 391 position is substituted by a member selected from the group consisting of Phe and Trp, and Gly at the 392 position is substituted by Pro.

6. A human antithrombin III mutant exhibiting elevated antithrombin activity, said human antithrombin III mutant having the identical amino acid sequence as that of human antithrombin III except that the following three mutations have occurred: either Arg at the 132 position is substituted by Gln or Lys at the 133 position is substituted by a member selected from the group consisting of Asn and Gln, Ala at the 391 position is substituted by Phe, and Gly at the 392 position is substituted by Pro.

7. A human antithrombin III mutant exhibiting elevated antithrombin activity, said human antithrombin III mutant having the identical amino acid sequence as that of human antithrombin III except that the following mutation has occurred: Arg at the 132 position is substituted by Gln, Lys at the 133 position is substituted by Asn and Gly at the 392 position is substituted by Pro or Arg at the 129 position is substituted by Gln, Ala at the 391 position is substituted by Phe and Gly at the 392 position is substituted by Pro.

8. A human antithrombin III mutant exhibiting elevated antithrombin activity, said human antithrombin III mutant having the identical amino acid sequence as that of human antithrombin III except that the following mutation has occurred: Arg at the 132 position is substituted by Gln, Lys at the 133 position is substituted by Asn, Ala at the 391 position is substituted by a member selected from the group consisting of Phe and Val, and Gly at the 392 position is substituted by Pro or Arg at the 132 position is substituted by Gln, Lys at the 133 position is substituted by Asn, Ile at the 390 position is substituted by Ala, and Ala at the 391 position is substituted by Leu.

9. A human antithrombin III mutant exhibiting elevated antithrombin activity, said human antithrombin III mutant having the identical amino acid sequence as that of human antithrombin III except that the following mutation has occurred: Lys at the 11 position is substituted by Ile, Asp at the 14 position is substituted by Ser, Ala at the 391 position is substituted by Phe, and Gly at the 392 position is substituted by Pro; Lys at the 125 position is substituted by Gln, Arg at the 132 position is substituted by Gln, Lys at the 133 position is substituted by Asn, Ala at the 391 position is substituted by Phe, and Gly at the 392 position is substituted by Pro; or Lys at the 125 position is substituted by Gln, Arg at the 129 position is substituted by Gln, Arg at the 132 position is substituted by Gln, Lys at the 133 position is substituted by Asn, Ala at the 391 position is substituted by Phe and Gly at the 392 position is substituted by Pro.

10. A human antithrombin III mutant as claimed in claim 4, wherein Lys at the 125 position is substituted by Gln, Ala at the 391 position is substituted by Phe and Gly at the 392 position is substituted by Pro.

11. A human antithrombin III mutant as claimed in claim 8, wherein Arg at the 132 position is substituted by Gln, Lys at the 133 position is substituted by Asn, Ala at the 391 position is substituted by Phe and Gly at the 392 position is substituted by Pro.

12. A human antithrombin III mutant as claimed in claim 3, wherein Ile at the 390 position is substituted by Ala and Ala at the 391 position is substituted by Leu.

13. A human antithrombin III mutant as claimed in claim 8, wherein Arg at the 132 position is substituted by Gln, Lys at the 133 position is substituted by Asn, Ile at the 390 position is substituted by Ala and Ala at the 391 position is substituted by Leu.

14. A human antithrombin III mutant as claimed in claim 6, wherein Arg at the 132 position is substituted by Gln, Ala at the 391 position is substituted by Phe and Gly at the 392 position is substituted by Pro.

15. A human antithrombin III mutant as claimed in claim 6, wherein Lys at the 133 position is substituted by Asn, Ala at the 391 position is substituted by Phe and Gly at the 392 position is substituted by Pro.

16. A human antithrombin III mutant as claimed in claim 6, wherein Lys at the 133 position is substituted by Gln, Ala at the 391 position is substituted by Phe and Gly at the 392 position is substituted by Pro.

* * * * *